US009082011B2

(12) United States Patent
Komogortsev

(10) Patent No.: US 9,082,011 B2
(45) Date of Patent: Jul. 14, 2015

(54) PERSON IDENTIFICATION USING OCULAR BIOMETRICS WITH LIVENESS DETECTION

(71) Applicant: Oleg V. Komogortsev, Austin, TX (US)

(72) Inventor: Oleg V. Komogortsev, Austin, TX (US)

(73) Assignee: Texas State University—San Marcos, San Marcos, TX (US)

( * ) Notice: Subject to any disclaimer, the term of this patent is extended or adjusted under 35 U.S.C. 154(b) by 92 days.

(21) Appl. No.: 13/908,748

(22) Filed: Jun. 3, 2013

(65) Prior Publication Data

US 2013/0336547 A1 Dec. 19, 2013

Related U.S. Application Data

(63) Continuation-in-part of application No. PCT/US2012/030912, filed on Mar. 28, 2012.

(51) Int. Cl.
G06K 9/00 (2006.01)
A61B 5/117 (2006.01)
A61B 5/16 (2006.01)
A61B 5/00 (2006.01)

(52) U.S. Cl.
CPC .............. G06K 9/0061 (2013.01); A61B 5/117 (2013.01); A61B 5/165 (2013.01); G06K 9/00335 (2013.01); G06K 9/00885 (2013.01); G06K 9/00899 (2013.01); A61B 5/4845 (2013.01)

(58) Field of Classification Search
CPC ...... A61B 5/117; A61B 5/165; A61B 5/4845; G06K 9/00899; G06K 9/00335; G06K 9/00885; G06K 9/0061
USPC ......................................................... 382/117
See application file for complete search history.

(56) References Cited

U.S. PATENT DOCUMENTS

| 4,669,834 A | 6/1987 | Richter |
| 5,682,210 A | 10/1997 | Weirich |

(Continued)

FOREIGN PATENT DOCUMENTS

| CN | 103544420 | 1/2014 |
| WO | 8907281 | 8/1989 |

OTHER PUBLICATIONS

Holland et al. "Biometric Identification via Eye Movement Scanpaths in Reading" Proceedings of the IEEE International Joint Conference on Biometrics (IJCB), 2011, pp. 1-8.

(Continued)

Primary Examiner — Shefali Goradia
(74) Attorney, Agent, or Firm — Meyertons, Hood, Kivlin, Kowert & Goetzel, P.C.; Eric B. Meyertons

(57) ABSTRACT

A method of assessing the identity of a person by one or more of: internal non-visible anatomical structure of an eye represented by the Oculomotor Plant Characteristics (OPC), brain performance represented by the Complex Eye Movement patterns (CEM), iris patterns, and periocular information. In some embodiments, a method of making a biometric assessment includes measuring eye movement of a subject, making an assessment of whether the subject is alive based on the measured eye movement, and assessing a person's identity based at least in part on the assessment of whether the subject is alive. In some embodiments, a method of making a biometric assessment includes measuring eye movement of a subject, assessing characteristics from the measured eye movement, and assessing a state of the subject based on the assessed characteristics.

20 Claims, 14 Drawing Sheets

(56) References Cited

U.S. PATENT DOCUMENTS

| | | | |
|---|---|---|---|
| 6,760,467 | B1 | 7/2004 | Min et al. |
| 7,346,195 | B2 | 3/2008 | Lauper et al. |
| 7,508,960 | B1 | 3/2009 | Bolle et al. |
| 7,797,040 | B2 * | 9/2010 | Pesaran et al. ............... 600/545 |
| 8,446,341 | B2 | 5/2013 | Amirparviz et al. |
| 8,602,789 | B2 * | 12/2013 | Hallowell et al. ............ 434/167 |
| 8,886,578 | B2 * | 11/2014 | Galiana et al. ................. 706/14 |
| 2001/0026632 | A1 | 10/2001 | Tamai et al. |
| 2003/0091215 | A1 | 5/2003 | Lauper et al. |
| 2005/0129286 | A1 | 6/2005 | Hekimian |
| 2012/0281181 | A1 | 11/2012 | Chen et al. |

OTHER PUBLICATIONS

Komogortsev et al. "Standardization of Automated Analyses of Oculomotor Fixation and Saccadic Behaviors" IEEE Transactions on Biomedical Engineering, vol. 57, No. 11, Nov. 2010, pp. 2635-2645.

Ceballos et al. "Ocular Imaging of Attentional Bias Among College Students: Automatic and Controlled Processing of Alcohol-Related Scenes" Journal of Studies on Alcohol and Drugs, 2009, pp. 652-659, 2009.

Komogortsev "Gaze-Contingent Video Compression with Targeted Gaze Containment Performance" Journal of Electronic Imaging, 18 (33), pp. 1-10, 2009.

Fuhrmann et al. "Investigating Hologram-based Route Planning. Transactions of Geographical Information Science" 13 (1), pp. 177-196, 2009.

Komogortsev et al. "Eye Movement Prediction by Oculomotor Plant Kalman Filter with Brainstem Control" Journal of Control Theory and Applications, 7 (1), pp. 14-22, 2009.

Komogortsev et al. "Quick Models for Saccade Amplitude Prediction" Journal of Eye Movement Research, 3 (1), pp. 1-13, 2009.

Komogortsev et al. "Predictive Real-Time Perceptual Compression Based on Eye-gaze-position Analysis" ACM Transactions on Multimedia Computing, Communications and Applications Journal, 5 (1), Feb. 2009.

Khan et al. "A Hybrid Scheme for Perceptual Object Window Design with Joint Scene Analysis and Eye-Gaze Tracking for Media Encoding based on Perceptual Attention" Journal of Electronic Imaging, 15(02), pp. 1-12, 2006.

Brooks et al. User Centered Design and Evaluation of an Eye Movement-based Biometric Authentication System, In Proceedings of the ACM Symposium on Usable Privacy and Security, pp. 1-2, 2011.

Sewell et al. "Real Time Eye Gaze Tracking With an Unmodified Commodity Webcam Employing a Neural Network" Proceedings of ACM Conference on Human Factors in Computing Systems (CHI), Atlanta, GA, 2010, pp. 1-6.

Gowda et al. "Real Time Eye Movement Identification Protocol" Proceedings of ACM Conference on Human Factors in Computing Systems (CHI), Atlanta, GA, 2010, pp. 1-6.

Komogortsev et al. Qualitative and Quantitative Scoring and Evaluation of the Eye Movement Classification Algorithms. In Proceedings of ACM Eye Tracking Research & Applications Symposium, Austin, TX, 2010, pp. 1-4.

Komogortsev et al. "Biometric Identification via an Oculomotor Plant Mathematical Model" Proceedings of ACM Eye Tracking Research & Applications Symposium, Austin, TX, 2010, pp. 1-4.

Komogortsev et al. "Instantaneous Saccade Driven Eye Gaze Interaction" In Proceedings of ACM International Conference on Advances in Computer Entertainment Technology, 2009 pp. 1-8.

Feldman et al. "Usability Testing with Total-Effort Metrics" Proceedings of ACM Symposium on Empirical Software Engineering and Measurement (ESEM) Lake Buena Vista, FL, 2009, pp. 426-429.

Mueller et al. "Using Designer's Effort for User Interface Evaluation" Proceedings of IEEE International Conference on Systems, Man, and Cybernetics San Antonio, Texas, USA: IEEE, 2009, pp. 1-6.

Koh et al. "Input Evaluation of an Eye-Gaze-Guided Interface: Kalman Filter vs. Velocity Threshold Eye Movement Identification" Proceedings of of the ACM SIGCHI symposium on engineering interactive computing systems (EICS 2009), Jul. 2009.

Komogortsev et al. "An Effort Based Model of Software Usability" Proceedings of the International Conference on Software Engineering Theory and Practice (SETP 2009), Jul. 2009.

Komogortsev et al. "2D Oculomotor Plant Mathematical Model for Eye Movement Simulation" Proceedings of the 8th IEEE International Conference on Bioinformatics and Bioengineering (BIBE), Oct. 2008.

Tamir et al. "An Effort and Time Based Measure of Usability" In Proceedings of the 6th international Workshop on Software Quality (WoSQ 2008), May 2008. pp. 1-6.

Komogortsev et al. "Eye Movement Prediction by Kalman Filter with Integrated Linear Horizontal Oculomotor Plant Mechanical Model" Proceedings of the Eye Tracking Research & Applications Symposium (ETRA 2008), Mar. 2008. pp. 229-236.

Komogortsev et al. "Kalman Filtering in the Design of Eye-Gaze-Guided Computer Interfaces" Proceedings of the 12th International Conference on Human-Computer Interaction (HCI 2007), Beijing, China, Jul. 22-27, 2007. pp. 679-689.

Komogortsev et al. "Perceptual Multimedia Compression Based on the Predictive Kalman Filter Eye Movement Modeling" Proceedings of the Multimedia Computing and Networking (MMCN 2007), San Jose, California, Jan. 28-Feb. 1.

Komogortsev et al. "Perceptual Attention Focus Prediction for Multiple Viewers in Case of Multimedia Perceptual Compression with Feedback Delay" Proceedings of the Eye Tracking Research & Applications Symposium (ETRA 06), San Diego, Mar. 27-29, 2006, pp. 101-108.

Komogortsev et al. "Perceptual Media Compression for Multiple Viewers with Feedback Delay" Proceedings of the 13th ACM International conference on Multimedia (ACM MM 2005), Singapore, Nov. 6-1, 2005, pp. 796-797.

Komogortsev et al. "Predictive Perceptual Compression for Real Time Video Communication" Proceedings of the 12th ACM International conference on Multimedia (ACM MM 2004), New York, Oct. 10-16, 2004, pp. 220-227.

Komogortsev et al. "Contour Approximation for Faster Object based Transcoding with Higher Perceptual Quality" Proceedings of the Computer Graphics and Imaging (CGIM 2004), Kauai, Hawaii, Aug. 17-19, 2004, ISBN 0-88986-418-7, pp. 441-446.

Khan et al. "Perceptual Video Compression with Combined Scene Analysis and Eye-Gaze Tracking" Proceedings of the Eye Tracking Research & Applications Symposium (ETRA 2004), San Antonio, Texas, Mar. 22-24, 2004, pp. 57-57.

Khan et al. A Hybrid Scheme for Perceptual Object Window Design with Joint Scene Analysis and Eye-Gaze Tracking for Media Encoding based on Perceptual Attention. In Proceedings of the IS&T/ SPIE Symposium of Visual Communications and Image Processing 2004 (EI04) Electronic Imaging 2004, SPIE vol. 5308, San Jose, California, Jan. 18-22, 2004, pp. 1341-1352.

Khan et al. "Resource Adaptive Netcentric Systems on Active Network: a Self-Organizing Video Stream that Automorphs itself while in Transit Via a Quasi-Active Network. In Proceedings of the Active Networks Conference and Exposition (DANCE '2002)" IEEE Computer Society Press, San Francisco, California, May 29-31, 2002, ISBN: 0-7695-1564-9, pp. 409-426.

Khan et al. "Resource Adaptive Netcentric Systems: A case Study with SONET—a Self-Organizing Network Embedded Transcoder." Proceedings of the 9th ACM International conference on Multimedia (ACM MM 01), Ottawa, Canada, Sep. 30-Oct. 5, 2001, ISBN:1-58113-394-4, pp. 617-620.

International Search Report for PCT Application No. PCT/US2012/030912 issued Nov. 27, 2012.

International Preliminary Report on Patentability for PCT Application No. PCT/US2012/030912 issued Nov. 27, 2012.

Komogortsev et al. "Biometric Authentication via Anatomical Characteristics of the Oculomotor Plant" Technical Report TR2011-07-25, Texas State University, Jul. 2011.

* cited by examiner

PERSON IDENTIFICATION USING OCULAR BIOMETRICS WITH LIVENESS DETECTION

PRIORITY CLAIM

This application is a continuation-in-part of International Application No. PCT/US2012/30912 Entitled: "PERSON IDENTIFICATION USING OCULAR BIOMETRICS", filed on Mar. 28, 2012, the disclosure of which is incorporated herein by reference in its entirety.

STATEMENT REGARDING FEDERALLY SPONSORED RESEARCH OR DEVELOPMENT

This invention was made with government support under award no. 60NANB10D213 awarded by the National Institute of Standards, the National Science Foundation CAREER Grant #CNS-1250718, the National Institute of Standards and Technology Grants #60NANB10D213 and #60NANB12D234, and the National Science Foundation GRFP Grant #DGE-1144466. The government has certain rights in the invention.

BACKGROUND

1. Field

This disclosure is generally related to person identification, and more specifically to methods and systems for identifying persons using ocular biometric information.

2. Description of the Related Art

Accurate, non-intrusive, and fraud-resistant identity recognition is an area of increasing concern in today's networked world, with the need for security set against the goal of easy access. Many commonly used methods for identity determination have known problems. For example, password verification has demonstrated many weaknesses in areas of accuracy (the individual typing the password may not actually be its owner), usability (people forget passwords), and security (people write passwords down or create easy-to-hack passwords).

The communication between a human and a computer frequently begins with an authentication request. During this initial phase of interaction a user supplies a system with verification of his/her identity, frequently given in the form of a typed password, graphically encoded security phrase, or a biometric token such as an iris scan or fingerprint. In cases when the user is prompted to select the identification key from a sequence of numerical and graphical symbols, there is a danger of accidental or intentional shoulder surfing performed directly or by use of a hidden camera. Moreover, such challenges may become specifically pronounced in cases of multi-user environments including shared-workstation use and more contemporary interaction media such as tabletops. Authentication methods requiring remembrance of information such as symbols and photos have reduced usability, due to the fact that long, sophisticated passwords can be easily forgotten and short passwords are easy to break. Even biometric methods such as iris and finger print-based authentication may not be completely fraud-proof, since they are based on a human's body characteristics that can be replicated.

There are a number of methods employed today for biometric purposes. Some examples include the use of fingerprints, iris, retina scans, face recognition, hand/finger geometry, brain waves, periocular features, ear shape, gait, and voice recognition. Iris-based identification is considered to be one of the most accurate among existing biometric modalities. However, commercial iris-identification systems may be easy to spoof, and they are also inconvenient and intrusive since they usually require a user to stand very still and very close to the image capturing device.

The human eye includes several anatomical components that make up the oculomotor plant (OP). These components include the eye globe and its surrounding tissues, ligaments, six extraocular muscles (EOMs) each containing thin and thick filaments, tendon-like components, various tissues and liquids.

The brain sends a neuronal control signal to three pairs of extraocular muscles, enabling the visual system to collect information from the visual surround. As a result of this signal, the eye rotates in its socket, exhibiting eye movement such as the following types: fixation, saccade, smooth pursuit, optokinetic reflex, vestibulo-ocular reflex, and vergence. In a simplified scenario, when a stationary person views a two-dimensional display (e.g., computer screen), three eye movement types are exhibited: fixations (maintaining the eye directed on the stationary object of interest), saccades (rapid eye rotations between points of fixation with velocities reaching 700°/s), and smooth pursuit (movements that occur when eyes are tracking a smooth moving object).

Accurate estimation of oculomotor plant characteristics is challenging due to the secluded nature of the corresponding anatomical components, which relies on indirect estimation and includes noise and inaccuracies associated with the eye tracking equipment, and also relies on effective classification and filtering of the eye movement signal.

In some cases, an intruder may carry out a coercion attack in which a genuine user is forced to log into a secure terminal (e.g., using a remote connection) under duress. Some approaches for preventing coercive attacks are easily observable (for example, typed passwords or voice commands), or intrusive (for example, skin conductance sensors).

Many biometric technologies are susceptible to attacks in which faked human features (for example, fake fingerprints, facial images, or iris images) are successfully as passed off as authentic. For example, some commercial iris-identification systems can be spoofed by high resolution images printed on placards with small holes in the images to bypass liveness tests, fingerprints can be spoofed with common household articles such as gelatin, and face recognition systems can be spoofed with printed face images. In certain cases, a spoofing attack involves presenting an accurate mechanical replica of the human eye is presented to the sensor. Such replicas may perform the eye movements similar to that of a human.

SUMMARY

In an embodiment, a multi-modal method of assessing the identity of a person includes measuring eye movement of the person and measuring characteristics of an iris or/and periocular information of a person. Based on measured eye movements, estimates may be made of characteristics of an oculomotor plant of the person, complex eye movement patterns representing brain's control strategies of visual attention, or both. Complex eye movement patterns may include, for example, a scanpath of the person's eyes including a sequence of fixations and saccades. The person's identity may be assessed based on the estimated characteristics of the oculomotor plant, the estimated complex eye movement patterns, and the characteristics of the iris of the person or/and periocular information. The identity assessment may be used to authenticate the person (for example, to allow the person access to a computer system or access to a facility).

In an embodiment, a method of assessing a person's identity includes measuring eye movements of the person. Based on measured eye movements, estimates are made of characteristics of an oculomotor plant of the person and complex eye movement patterns of the person's eyes. The person's identity may be assessed based on the estimated characteristics of the oculomotor plant and the estimated complex eye movement patterns that are representative of the brain's control strategies of visual attention.

In an embodiment, a method of assessing a person's identity includes measuring eye movements of the person while the person is looking at stimulus materials. In various embodiments, for example, the person may be reading, looking at various pictures, or looking at a jumping dot of light. Estimates of characteristics of an oculomotor plant are made based on the recorded eye movements.

In an embodiment, a system for assessing the identity of a person includes a processor, a memory coupled to the processor, and an instrument (e.g. image sensor such as web-camera) that can measure eye movement of a person and external ocular characteristics of the person (such as iris characteristics or periocular information). Based on measured eye movements, the system can estimate characteristics of an oculomotor plant of the person, strategies employed by the brain to guide visual attention represented via complex eye movement patterns, or both. The system can assess the person's identity based on the estimated characteristics of the oculomotor plant, brain strategies to guide visual attention via complex eye movement patterns, and the external ocular characteristics of the person.

In an embodiment, a method of making a biometric assessment includes measuring eye movement of a subject, making an assessment of whether the subject is alive based on the measured eye movement, and assessing a person's identity based at least in part on the assessment of whether the subject is alive.

In an embodiment, a method of making a biometric assessment includes measuring eye movement of a subject, assessing characteristics from the measured eye movement, and assessing a state of the subject based on the assessed characteristics.

Figure 1:
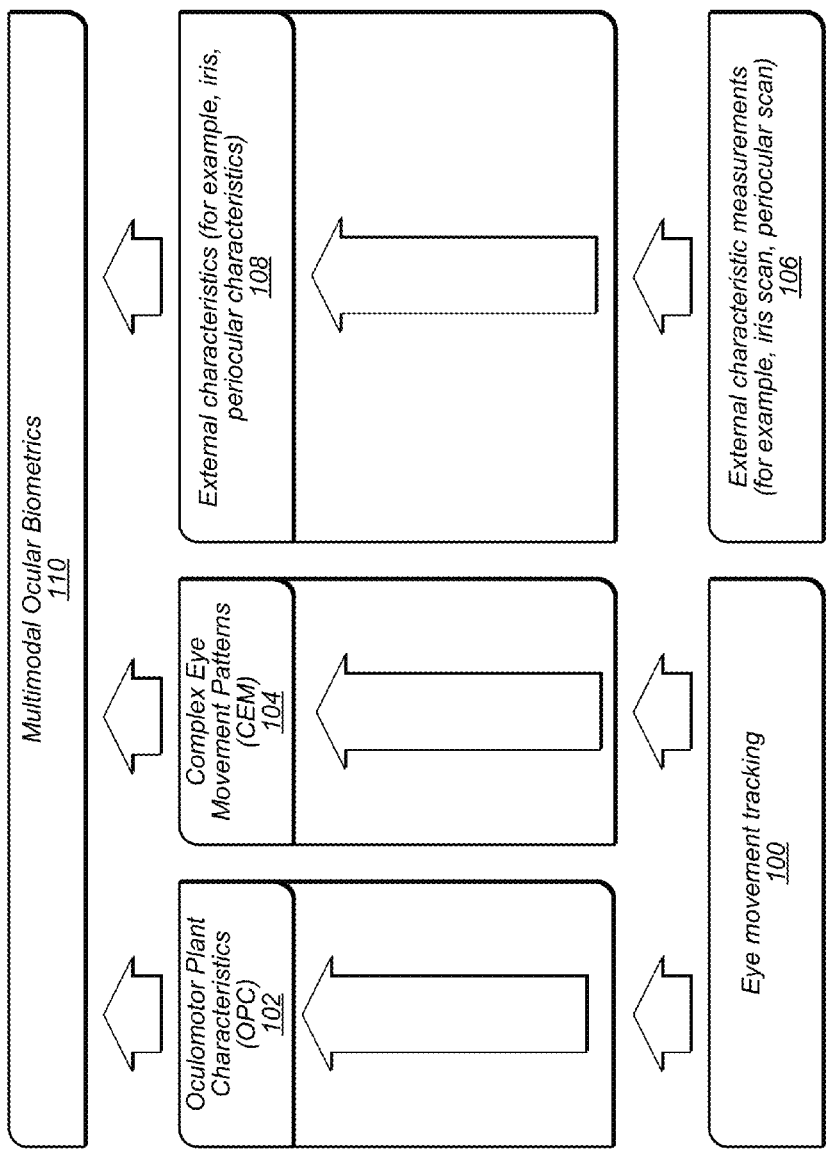
FIG. 1 illustrates one embodiment of assessing a person's identity using multimodal ocular biometrics based on eye movement tracking and measurement of external characteristics.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

As used herein, "oculomotor plant" means the eye globe and its surrounding tissues, ligaments, and extraocular muscles (EOMs), each of which may contain thin and thick filaments, tendon-like components, various tissues and liquids.

As used herein, "scanpath" means a spatial path formed by a sequence of fixations and saccades. Fixations occur when the eye is held in a relatively stable position, allowing heightened visual acuity on an object of interest. Saccades may occur when the eye rotates quickly, for example, between points of fixation, with almost no visual acuity maintained during rotation. Velocities during saccades may reach as high as 700° per second.

As used herein, "brain control strategies" are defined as an ability of the brain to guide the eye to gather the information from the surrounding world. Strategies may be based on, or include, information on how and where the eye is guided. Brain control strategies can manifest themselves in the spatial and temporal (e.g. location and duration) characteristics of fixation, such characteristics of saccades as main-sequence relationship (relationship between maximum velocity exhibited during a saccade and its amplitude), amplitude duration relationship (relationship between saccade's duration and its amplitude), saccade's waveform (relationship between the time it takes to reach a peak velocity during a saccade to the total saccade duration) and other characteristics.

As used herein, "complex eye movement (CEM) patterns" are defined as eye movement patterns and characteristics that allow inferring brain's strategies or activity to control visual attention. This information might be inferred from individual and aggregated characteristics of a scanpath. In addition CEM can include, for example, the information about saccades elicited in response to different stimuli. Examples of forms in which CEM information may be manifested include: simple undershoot or overshoot (e.g. saccades that miss the target and no correction is made to put gaze location on the target), corrected undershoot/overshoot (e.g. saccades that miss the target, but the brain corrects eye position to the target's position), multi-corrected undershoot/overshoot— similar in definition to the corrected undershoot/overshoot saccade however additional series of corrective saccades is added that brings the resulting fixation position closer to the target; dynamic overshoot which is the oppositely directed post-saccadic eye movement in the form of backward jerk at the offset of a saccade; compound saccade which represented by an initial saccade that is subsequently followed by two or more oppositely directed saccades of small amplitude that move the eye-gaze back and forth from the target position; and express saccade which is represented by a sequence of saccades directed toward the target where the end of the initial saccade is in the small spatial and temporal proximity from the sequence of new saccades leading to the target.

As used herein, "assessing a person's identity" includes determining that a person being assessed or measured is a particular person or within a set or classification or persons. "Assessing a person's identity" also includes determining that a person being assessed is not a particular person or within a set or classification or persons (for example, scanning eye movements of Person X to determine whether or not Person X is on a list a persons authorized to access to a computer system).

In some embodiments, a person's identity is assessed using one or more characteristics that exist only in a live individual. The assessment may be used, for example, to authenticate the person for access to a system or facility. In certain embodiments, authentication of a person does not require the person being authenticated to remember any information (for example, to remember a password).

In some embodiments, a person's identity is assessed using measurements of one or more visible characteristics of the person in combination with estimates of one or more non-visible characteristics of the person. The assessment may be used to authenticate the person for access a computer system, for example.

In some embodiments, a method of assessing a person's identity includes making estimates based on eye movements of a person and measuring iris characteristics or periocular information of the person. Eye movements may be used to estimate oculomotor plant characteristics, brain control strategies in a form of complex eye movement patters and scanpaths, or all these characteristics. FIG. 1 illustrates one embodiment of assessing a person's identity using multimodal ocular biometrics based on eye movement tracking and measurement of external characteristics. At 100, eye movements of a person are tracked. Eye movement data may be collected using, for example, an eye tracking instrument.

At 102, acquired eye movement data may be used to estimate oculomotor plant characteristics. Dynamic and static characteristics of the oculomotor plant that may be estimated include the eye globe's inertia, dependency of an individual muscle's force on its length and velocity of contraction, resistive properties of the eye globe, muscles and ligaments, characteristics of the neuronal control signal sent by the brain to the EOMs, and the speed of propagation of this signal. Individual properties of the EOMs may vary depending on their roles. For example, the agonist role may be associated with the contracting muscle that pulls the eye globe in the required direction, while the antagonist role may be associated with the lengthening muscle resisting the pull.

At 104, acquired eye movement data may be used to analyze complex eye movements. The CEM may be representative of the brain's control strategies of guiding visual attention. Complex eye movement patterns may be based on, for example, on individual or aggregated scanpath data. Scanpaths may include one or more fixations and one or more saccades by a person's eye. The processed fixation and saccade groups may describe the scanpath of a recording. Individual scanpath metrics may be calculated for each recording based on the properties of its unique scanpath. Basic eye movement metrics may include: fixation count, average fixation duration, average vectorial average vertical saccade amplitude, average vectorial saccade velocity, average vectorial saccade peak velocity, and the velocity waveform indicator (Q), and a variety of saccades such as: undershot/overshoot, corrected undershoot/overshoot, multi-corrected undershoot/overshoot, dynamic, compound, and express saccades. More complex metrics, resulting from the aggregated scanpath data, may include: scanpath length, scanpath area, regions of interest, inflection count, and slope coefficients of the amplitude-duration and main sequence relationships.

At 106, measurements may be taken of external characteristics of the person. In one embodiment, one or more characteristics of the person's iris or/and periocular information are measured. In certain embodiments, non-ocular external characteristics, such as a facial characteristics or fingerprints, may be acquired in addition to, or instead of external ocular characteristics. At 108, the measurements acquired at 106 are used to assess external characteristics of a person.

At 110, a biometric assessment is performed based on some or all of the estimated oculomotor plant characteristics, complex eye movement patterns, and external ocular characteristics. In some embodiments, biometric assessment is based on a combination of one or more dynamic characteristics is combined with one or more static traits, such as iris patterns or periocular information. Authentication of a person may be carried out based on a combination of two or more of: oculomotor plant characteristics, complex eye movement patterns, and external ocular characteristics.

In some embodiments, a single instrument is used to acquire all of the eye movement data and external characteristic data (for example, iris patterns or/and periocular information) for a person. In other embodiments, two or more different instruments may be used to acquire eye movement data or external characteristic data for a person.

Methods and systems as described herein may be shoulder-surfing resistant. For example, data presented during authentication procedures as described herein may not reveal any information about a user to an outside observer. In addition, methods and systems as described herein may be counterfeit-resistant in that, for example, they can be based on internal non-visible anatomical structures or complex eye movement patters representative of the brain's strategies to guide visual attention. In some embodiments, information on OPC and CEM biometric used in combination with one another to assess identity of a person.

In some embodiments, a user is authenticated by estimating individual oculomotor plant characteristics (OPC) and complex eye movement patterns generated for a specific type of stimulus. The presented visual information may be used to evoke eye movements that facilitate extraction of the OPC and CEM. The information presented can be overseen by a shoulder-surfer with no negative consequences. As a result, the authentication does not require any feedback from a user except looking at a presented sequence of images or text.

Figure 2:
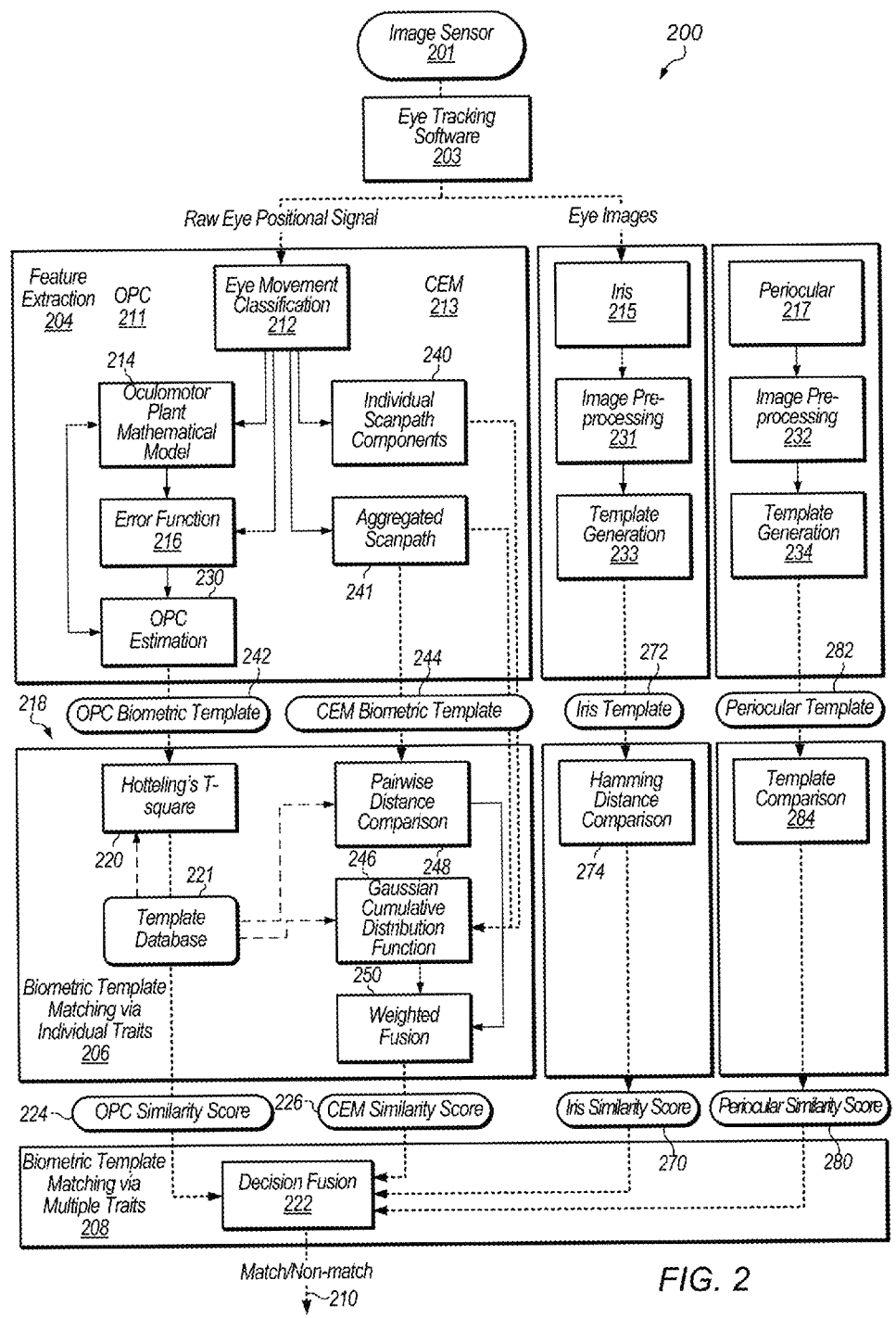
FIG. 2 illustrates one embodiment of authentication using oculomotor plant characteristics, complex eye movement patterns, iris and periocular information.

FIG. 2 illustrates one embodiment of authentication using OPC, CEM, iris, and periocular information. The OPC, CEM, iris, and periocular information may be captured by a single camera sensor. Identity assessment 200 includes use of image sensor 201 and eye tracking software 203. From image data captured with image sensor 201, eye tracking software 203 may generate raw eye positional signal data, which may be sent to the OPC and the CEM modules, and eye images, which may be sent to iris module 205 and periocular module 207. In general, all modules may process the input in the form of raw eye position signal or eye images, perform feature extraction, generate biometric templates, perform individual trait template matching 206, multi-trait template matching phase 208, and decision output 210. Feature extraction 204 includes OPC feature extraction 211, CEM feature extraction 213, iris feature extraction 215, and periocular feature extraction 217. Processing of eye images includes iris module image pre-processing 231, periocular module image pre-processing 232, iris module template generation 233, At 202, eye positional signal information is acquired. Raw eye movement data produced during a recording is supplied to an eye movement classification module at 212. In some embodiments, an eye-tracker sends the recorded eye gaze trace to an eye movement classification algorithm at 212 after visual information employed for the authentication is presented to a user. An eye movement classification algorithm may extract fixations and saccades from the signal. The extracted saccades' trajectories may be supplied to the mathematical model of the oculomotor plant 214 for the purpose of simulating the exact same trajectories. At 216, an optimization algorithm modifies the values for the OPC to produce a minimum error between the recorded and the simulated signal. The values that produce the minimum error are supplied to an authentication algorithm at 218. The authentication algorithm may be driven by a Hotteling's T-square test 220. Templates may be accessible from template database 221. The Hotteling's T-square test (or some other appropriate statistical test) may either accept or reject the user from the system. An authentication probability value (which may be derived, for example, by the Hotteling's T-square test) may be propagated to decision fusion module 222. Although in the embodiment shown in FIG. 2, a Hotteling's T-square test is employed, an authentication algorithm may be driven by other suitable statistical tests. In one embodiment, an authentication algorithm uses a Student's t-test is used (which may be enhanced by voting).

Fusion module 222 may accept or reject a person based on one or more similarity scores. In some case, fusion module 222 accept or reject a person based on OPC similarity score 224, CEM similarity score 226, iris similarity score 270, and periocular similarity score 280. Further aspects of implementing authentication based on OPC and the other modalities are set forth below.

Eye Movement Classification: At 212, a Velocity-Threshold (I-VT) classification algorithm (or some other eye movement classification algorithm) may be employed with threshold selection accomplished via standardized behavior scores. After the classification saccades with amplitudes smaller than 0.5° (microsaccades) may be filtered out to reduce the amount of noise in the recorded data.

Oculomotor Plant Mathematical Model: At 214, a linear horizontal homeomorphic model of the oculomotor plant capable of simulating the horizontal and vertical component of eye movement during saccades may be employed. The model mathematically may represent dynamic properties of the OP via a set of linear mechanical components such as springs and damping elements. The following properties may be considered for two extraocular muscles that are modeled (medial and lateral recti) and the eye globe: active state tension—tension developed as a result of the innervations of an EOM by a neuronal control signal, length tension relationship—the relationship between the length of an EOM and the force it is capable of exerting, force velocity relationship—the relationship between the velocity of an EOM extension/contraction and the force it is capable of exerting, passive elasticity—the resisting properties of an EOM not innervated by the neuronal control signal, series elasticity—resistive properties of an EOM while the EOM is innervated by the neuronal control signal, passive elastic and viscous properties of the eye globe due to the characteristics of the surrounding tissues. The model may take as an input a neuronal control signal, which may be approximated by a pulse-step function. The OPC described above can be separated into two groups, each separately contributing to the horizontal and the vertical components of movement.

OPC Estimation Algorithm: At 230, a Nelder-Mead (NM) simplex algorithm (or some other minimization algorithm such as Trust-Region using the interior-reflective Newton method) may be used in a form that allows simultaneous estimation of all OPC vector parameters at the same time. A subset of some OPC may be empirically selected. The remaining OPC may be fixed to default values. In an example a subset of selected OPC comprises of length tension—the relationship between the length of an extraocular muscle and the force it is capable of exerting, series elasticity—resistive properties of an eye muscle while the muscle is innervated by the neuronal control signal, passive viscosity of the eye globe, force velocity relationship—the relationship between the velocity of an extraocular muscle extension/contraction and the force it is capable of exerting—in the agonist muscle, force velocity relationship in the antagonist muscle, agonist and antagonist muscles' tension intercept that ensures an equilibrium state during an eye fixation at primary eye position (for example an intercept coefficient in a linear relationship between the force that a muscle applies to the eye and the rotational position of the eye during fixation), the agonist muscle's tension slope (for example, a slope coefficient in a linear relationship between the force that an agonist muscle applies to the eye and the rotation position of the eye during fixation), the antagonist muscle's tension slope (for example, a tension slope coefficient for the antagonist muscle), and eye globe's inertia. Lower and upper boundaries may be imposed to prevent reduction or growth of each individual OPC value to less than 10% or larger than 1000% of its default value. Stability degradation of the numerical solution for differential equations describing the OPMM may be used as an additional indicator for acceptance of the suggested OPC values by the estimation algorithm. In some embodiments, a template including some or all of the OPC described above is passed to a matching module to produce a matching score between a computed template and a template already stored in the database.

Authentication: As an input, the person authentication algorithm takes a vector of the OPC optimized for each qualifying saccade. In some embodiments, a statistical test is applied to assess all optimized OPC in the vector at the same time. In the example shown in FIG. 2, a Hotelling's T-square test is applied. The test may assess data variability in a single individual as well as across multiple individuals. In one embodiment, the Hotelling's T-square test is applied to an empirically selected subset of five estimated parameters: series elasticity, passive viscosity of the eye globe, eye globe's inertia, agonist muscle's tension slope, and the antagonist muscle's tension slope.

As a part of the authentication procedure, the following Null Hypothesis (H0) is formulated assuming datasets i and j may be compared: "H0: There is no difference between the vectors of OPC between subject i and j". The statistical significance level (p) resulting from the Hotelling's T-square test may be compared to a predetermined threshold (for example, 0.05). In this example, if the resulting p is smaller than the threshold, the H0 is rejected indicating that the datasets in question belonged to different people. Otherwise, the H0 is accepted indicating that the datasets belonged to the same person. Two types of errors may be recorded as a result: (1) the rejection test of the H0 when the datasets belonged to the same person; and (2) the acceptance test of the H0 when the datasets were from different people.

In the method described above, variability was accounted for by applying a Hotelling's T-square test. In certain embodiments, oculomotor plant characteristics are numerically evaluated given a recorded eye-gaze trace.

Referring to the CEM side of FIG. 2, aspects of biometrics using CEM are described. In some embodiments, some aspects of biometrics using CEM in a form of scanpaths are as described in C. Holland, and O. V. Komogortsev, Biometric Identification via Eye Movement Scanpaths in Reading, In Proceedings of the IEEE International Joint Conference on Biometrics (IJCB), 2011, pp. 1-8. As noted above, raw eye movement data produced during a recording is supplied to an eye movement classification module at 212. Classified fixations and saccades forming complex eye movement patterns may be processed by two modules: individual scanpath component module 240 and aggregated scanpath module 241. Individual scanpath component module 240 may process eye movement characteristics belonging to individual fixations and saccades. Characteristics processed by the individual scanpath component module 240 may include the following:

Fixation Count—number of detected fixations. Fixation count is indicative of the number of objects processed by the subject, and was measured simply as the total number of fixations contained within the scanpath.

Average Fixation Duration—sum of duration of all fixations detected divided by fixation count. Average fixation duration is indicative of the amount of time a subject spends interpreting an object, and was measured as the sum of fixation durations over the fixation count.

Average Vectorial Saccade Amplitude—sum of vectorial saccade amplitudes over the total number of saccades, where the vectorial amplitude of a saccade was defined as the Euclidean norm of the horizontal and vertical amplitudes. There is a noted tendency for saccades to maintain similar amplitudes during reading, average saccade amplitude was considered as a candidate biometric feature under the assumption that differences in amplitude may be apparent between subjects. Average vectorial saccade amplitude was measured as the sum of vectorial saccade amplitudes over the total number of saccades, where the vectorial amplitude of a saccade was defined as the Euclidean norm of the horizontal and vertical amplitudes, according to the equation:

$$\text{Vectorial Average} = \frac{\sum_{i=1}^{n} \sqrt{x_i^2 + y_i^2}}{n}$$

Average Horizontal Saccade Amplitude—average amplitude of the horizontal component of saccadic movement. Horizontal saccade amplitude was considered separately as these are more indicative of between-word saccades. Average horizontal saccade amplitude was measured as the sum of horizontal saccade amplitudes greater than 0.5° over the total number of horizontal saccades with amplitude greater than 0.5°.

Average Vertical Saccade Amplitude—average amplitude of the vertical component of saccadic movement. Vertical saccade amplitude was considered separately as these are more indicative of between-line saccades. Average vertical saccade amplitude was measured as the sum of vertical saccade amplitudes greater than 0.5° over the total number of vertical saccades with amplitude greater than 0.5°.

Average Vectorial Saccade Velocity—sum of vectorial saccade velocities over the total number of saccades, where the vectorial velocity of a saccade was defined as the Euclidean norm of the horizontal and vertical velocities. Average vectorial saccade velocity as measured as the sum of vectorial saccade velocities over the total number of saccades, where the vectorial velocity of a saccade was defined as the Euclidean norm of the horizontal and vertical velocities.

Average Vectorial Saccade Peak Velocity—sum of vectorial saccade peak velocities over the total number of saccades. Average vectorial saccade peak velocity was measured as the sum of vectorial saccade peak velocities over the total number of saccades, where the vectorial peak velocity of a saccade was defined as the Euclidean norm of the horizontal and vertical peak velocities.

Velocity Waveform Indicator (Q)—the relationship between the time it takes to reach a peak velocity during a saccade to the total saccade duration. We use the term velocity waveform indicator (Q) to refer to the ratio of peak velocity to average velocity of a given saccade. In normal human saccades this value is roughly constant at 1.6, though it is assumed that this is subject to some amount of variation similar to the amplitude-duration and main sequence relationships. A rough estimate of this value may be obtained from the ratio of the average vectorial peak velocity over the average vectorial velocity.

Amplitude-Duration Relationship—the relationship between the amplitude of the saccade and its duration.

Coefficient of the Amplitude-Duration Relationship. The amplitude-duration relationship varies from person to person, and describes the tendency for saccade duration to increase linearly with amplitude, according to the equation:

$$\text{Duration} = C \times |\text{Amplitude}| + \text{Duration}_{min}$$

To calculate the slope coefficient of this relationship, a data set may be constructed from the saccade groups such that x-column data contained the larger absolute component (horizontal or vertical) amplitude and y-column data contained the respective saccade duration.

The slope coefficient of the amplitude-duration relationship may be obtained from a linear regression of this data set.

Main Sequence Relationship—the relationship between the amplitude of the saccade and its peak velocity.

Coefficient of the Main Sequence Relationship. The main sequence relationship varies from person to person, and describes the tendency for saccade peak velocity to increase exponentially with amplitude, according to the equation:

$$\text{Peak Velocity} = Velocity_{max}\left(1 - e^{\frac{|Amplitude|}{c}}\right)$$

This relationship has shown to be roughly linear for small saccades in the range of 0-10° amplitude. As a result, a linear approximation may be acceptable in the current context, as the saccades produced during reading are often on the order of 0-3° amplitude, with very few over 10° amplitude.

To calculate the slope coefficient of this relationship, a data set may be constructed from the saccade groups such that x-column data contained absolute component (horizontal or vertical) amplitude and y-column data contained the respective absolute component peak velocity. The slope coefficient of the main sequence relationship may be obtained from a linear regression of this data set.

Characteristics processed by the aggregated scanpath module 241 may include the following:

Scanpath Length—summated amplitude of all detected saccades. Scanpath length is indicative of the efficiency of visual search, and may be considered as a candidate biometric feature under the assumption that visual search is dependent on the subject's familiarity with similar patterns/content. Scanpath length may be measured as the sum of absolute distances between the vectorial centroid of fixation points, where the vectorial centroid was defined as the Euclidean norm of the horizontal and vertical centroid positions, according to the equation:

$$\text{Scanpath Length} = \Sigma_{i=2}^{n} |\sqrt{x_i^2 + y_i^2} - \sqrt{x_{i-1}^2 + y_{i-1}^2}|$$

Scanpath Area—area that is defined by a convex hull that is created by fixation points. Scanpath area may be measured as the area of the convex hull formed by fixation points. Scanpath area is similar to scanpath length in its indication of visual search efficiency, but may be less sensitive to localized searching. That is, a scanpath may have a large length while only covering a small area.

Regions of Interest—total number of spatially unique regions identified after applying a spatial mean shift clustering algorithm to the sequence of fixations that define a scanpath Regions of interest may be measured as the total number of spatially unique regions identified after applying a spatial mean shift clustering algorithm to the fixation points of the scanpath, using a sigma value of 2° and convergence resolution of 0.1°.

Inflection Count—number of eye-gaze direction shifts in a scanpath. Inflections occur when the scanpath changes direction, in reading there are a certain amount of "forced" inflections that may be necessary to progress through the text, but general differences in inflection count are indicative of attentional shifts. Inflection count may be measured as the number of saccades in which the horizontal and/or vertical velocity changes signs, according to the following algorithm:

1. Inflections=0
2. i=2
3. While i<Saccade Count:
4. If sign(Velocity$_i$)!=sign(Velocity$_{i-1}$):
5. Inflections=Inflections+1
6. End if
7. i=i+1
8. End while Scanpath$_{13}$ fix—aggregated representation of a scanpath that is defined by fixation points and their coordinates.

OPC biometric template 242 and scanpath biometric template 244 may be tested for match/non-match. Characteristics may be compared using Gaussian cumulative distribution function (CDF) 246. In some cases, all characteristics except the scanpath_fix are compared via Gaussian cumulative distribution function (CDF) 246.

To determine a relative measure of similarity between metrics, a Gaussian cumulative distribution function (CDF) was applied as follows, were x and μ are the metric values being compared and σ is the metric-specific standard deviation:

$$p = \frac{1}{\sigma\sqrt{2\pi}} \int_{-\infty}^{x} e^{-\frac{t-\mu}{2\sigma^2}} dt$$

A Gaussian CDF comparison produces a probability value between 0 and 1, where a value of 0.5 indicates an exact match and a value of 0 or 1 indicates no match. This probability may be converted into a more intuitive similarity score, where a value of 0 indicates no match and values of 1 indicates an exact match, with the following equation:

$$\text{Similarity} = 1 - |2p-1|$$

From the similarity score, a simple acceptance threshold may be used to indicate the level of similarity which constitutes a biometric match.

In some embodiments, scanpath_fix characteristics are compared via pairwise distances between the centroids representing positions of fixations at 248. In comparing two scanpaths, the Euclidean pairwise distance may be calculated between the centroid positions of fixations. Following this, a tally may be made of the total number of fixation points in each set that could be matched to within 1° of at least one point in the opposing set. The similarity of scanpaths may be assessed by the proportion of tallied fixation points to the total number of fixation points to produce a similarity score similar to those generated for the various eye movement metrics. In some embodiments, the total difference is normalized to produce a similarity score with a value of 0 indicates no match and values of 1 indicates an exact match.

Iris similarity score 270 may be generated using iris templates 272. In this example, to produce similarity score 270, a Hamming distance calculation is performed at 274.

Periocular similarity score 280 may be generated using periocular templates 282. Periocular similarity score 280 may be based periocular template comparisons at 284.

At 250, weighted fusion module produces a combined similarity score via a weighted sum of similarity scores produced by one or more of the individual metrics. Weights for each individual metrics may be produced empirically. Other score level fusion techniques can be applied, e.g., density-based score fusion techniques, transformation score fusion, classifier-based score fusion, methods that employ user-specific and evolving classification thresholds, and etc. The resulting similarity score may be employed for the decision of match/non-match for scanpath authentication or serves as an input to decision fusion module 222, which may combine, for example, OPC and CEM biometrics.

For example at 222, OPC similarity score 224 and CEM similarity score 226 may be considered for final match/non-match decisions. Match/non-match decisions may be made based on one or more of the following information fusion approaches:

Logical OR, AND. Logical fusion method employs individual decisions from the OPC and scanpath modalities in a form of 1 (match) or 0 (non-match) to produce the final match/non-match decision via logical OR (or AND) operations. In case of OR at least one method should indicate a match for the final match decision. In case of AND both methods should indicate a match for the final match decision.

MIN, MAX. For a MIN (or MAX) method, the smallest (or largest) similarity score may between the OPM and the scanpath modalities. Thresholding may be applied to arrive to the final decision. For example, if the resulting value is larger than a threshold a match is indicated; otherwise, a non-match is indicated.

Weighted addition. Weighted summation of the two or two similarity scores from the OPC, CEM, iris, and periocular may be performed via the formula $p=w_1 \cdot A + w_2 \cdot B + w_3 \cdot C + w_4 \cdot D$. Here p is the resulting score, A, B, C and B stands for scores derived from the OPC, CEM, Iris, and Periocular respectively. w1, w2, w3, w4 are corresponding weights. The resulting score p may be compared with a threshold value. If p is greater than the threshold, a match is indicated; otherwise, a non-match is indicated.

Other score level fusion techniques can be applied, e.g., density-based score fusion techniques, transformation score fusion, classifier-based score fusion, methods that employ user-specific and evolving classification thresholds, and etc.

Figure 3:
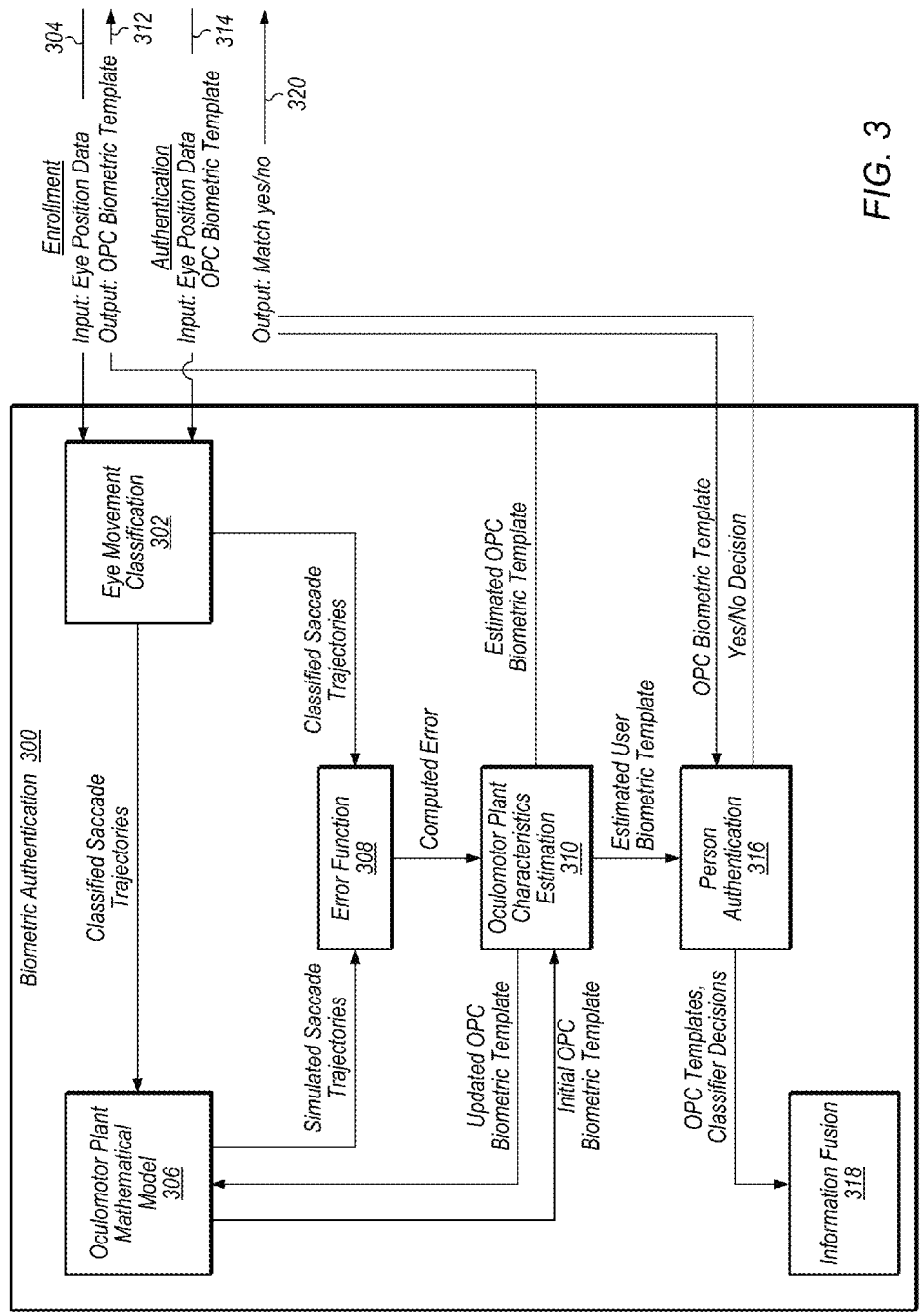
FIG. 3 is a block diagram illustrating architecture for biometric authentication via oculomotor plant characteristics according to one embodiment.

FIG. 3 is a block diagram illustrating architecture for biometric authentication via oculomotor plant characteristics according to one embodiment. In certain embodiments, assessment using OPC as described in FIG. 3 may be combined with assessments based on CEM, iris characteristics, periocular information, or some or all of those traits. In one embodiment, a biometric authentication is a based on a combination of OPC, CEM, iris characteristics, and periocular information.

Biometric authentication 300 may engage information during enrollment of a user and, at a later time, authentication of the user. During the enrollment, the recorded eye movement signal from an individual is supplied to the Eye movement classification module 302. Eye movement classification module 302 classifies the eye position signal 304 into fixations and saccades. A sequence of classified saccades' trajectories is sent to the oculomotor plant mathematical model (OPMM) 306.

Oculomotor plant mathematical model (OPMM) 306 may generate simulated saccades' trajectories based on the default OPC values that are grouped into a vector with the purpose of matching the simulated trajectories with the recorded ones. Each individual saccade may be matched independently of any other saccade. Both classified and simulated trajectories for each saccade may be sent to error function module 308. Error function module 308 may compute error between the trajectories. The error result may trigger the OPC estimation module 310 to optimize the values inside of the OPC vector minimizing the error between each pair of recorded and simulated saccades.

When the minimum error is achieved for all classified and simulated saccade pairs, an OPC biometric template 312 representing a user may be generated. The template may include a set of the optimized OPC vectors, with each vector representing a classified saccade. The number of classified saccades may determine the size of the user's OPC biometric template.

During a person's verification, the information flow may be similar to the enrollment procedure. Eye position data 314 may be provided to eye movement classification module 302. In addition, the estimated user biometrics template may be supplied to the person authentication module 316 and information fusion module 318 to authenticate a user. Person authentication module 316 may accept or reject a user based on the recommendation of a given classifier. Information fusion module 318 may aggregate information related to OPC vectors. In some embodiments, information fusion module 318 may work in conjunction with the person authentication module to authenticate a person based on multiple classification methods. The output during user authentication procedure may be a yes/no answer 320 about claimed user's identity.

Further description for various modules in this example is provided below.

Figure 4:
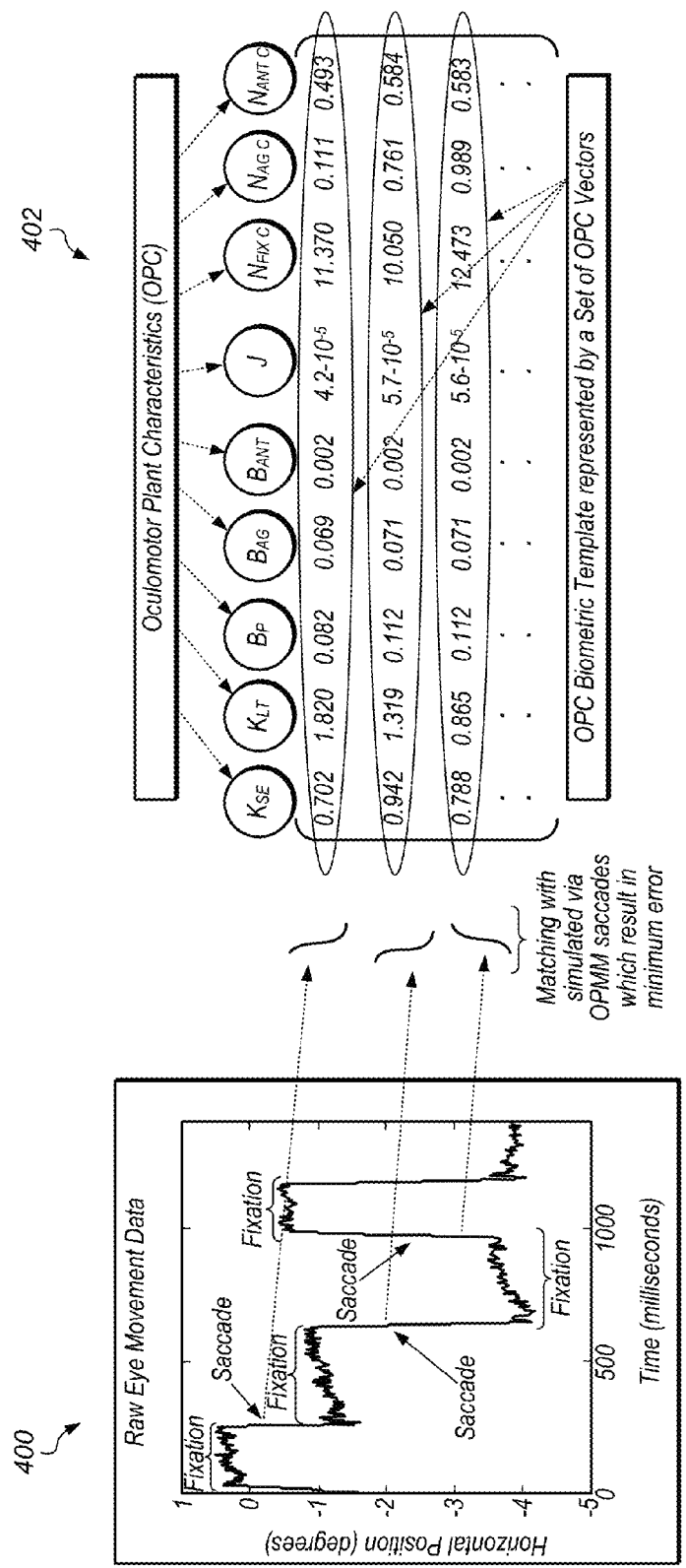
FIG. 4 illustrates raw eye movement signal with classified fixation and saccades and an associated oculomotor plant characteristics biometric template.

Eye Movement Classification. An automated eye movement classification algorithm may be used to help establish an invariant representation for the subsequent estimation of the OPC values. The goal of this algorithm is to automatically and reliably identify each saccade's beginning, end and all trajectory points from a very noisy and jittery eye movement signal (for example, as shown in FIG. 4. The additional goal of the eye movement classification algorithm is to provide additional filtering for saccades to ensure their high quality and a sufficient quantity of data for the estimation of the OPC values.

In one embodiment, a standardized Velocity-Threshold (I-VT) algorithm is selected due to its speed and robustness. A comparatively high classification threshold of 70° per second may be employed to reduce the impact of trajectory noises at the beginning and the end of each saccade. Additional filtering may include discarding saccades with amplitudes of less than 4°/s, duration of less than 20 ms, and various trajectory artifacts that do not belong to normal saccades.

Oculomotor Plant Mathematical Model. The oculomotor plant mathematical model simulates accurate saccade trajectories while containing major anatomical components related to the OP. In one embodiment, a linear homeomorphic 2D OP mathematical model is selected. The oculomotor plant mathematical model may be, for example, as described in O. V. Komogortsev and U. K. S. Jayarathna, "2D Oculomotor Plant Mathematical Model for eye movement simulation," in *IEEE International Conference on BioInformatics and Bioengineering (BIBE)*, 2008, pp. 1-8. The oculomotor plant mathematical model in this example is capable of simulating saccades with properties resembling normal humans on a 2D plane (e.g. computer monitor) by considering physical properties of the eye globe and four extraocular muscles: medial, lateral, superior, and inferior recti. The following advantages are associated with a selection of this oculomotor plant mathematical model: 1) major anatomical components are accounted for and can be estimated, 2) linear representation simplifies the estimation process of the OPC while producing accurate simulation data within the spatial boundaries of a regular computer monitor, 3) the architecture of the model allows dividing it into two smaller 1D models. One of the smaller models becomes responsible for the simulation of the horizontal component of movement and the other for the vertical. Such assignment, while producing identical simulation results when compared to the full model, may allow a significant reduction in the complexity of the required solution and allow simultaneous simulation of both movement components on a multi-core system.

Specific OPC that may be accounted by the OPMM and selected to be a part of the user's biometric template are discussed below. FIG. 4 illustrates raw eye movement signal with classified fixation and saccades 400 and an associated OPC biometric template 402. In the middle of FIG. 4, simulated via OPMM saccade trajectories generated with the OPC vectors that provide the closest matches to the recorded trajectories are shown.

In this example, a subset of nine OPC is selected as a vector to represent an individual saccade for each component of movement (horizontal and vertical). Length tension (Klt=1.2 g/°)—the relationship between the length of an extraocular muscle and the force it is capable of exerting, series elasticity (Kse=2.5 g/°)—resistive properties of an eye muscle while the muscle is innervated by the neuronal control signal, passive viscosity (Bp=0.06 g.s/°) of the eye globe, force velocity relationship—the relationship between the velocity of an extraocular muscle extension/contraction and the force it is capable of exerting—in the agonist muscle (BAG=0.046 g-s/°), force velocity relationship in the antagonist muscle (BANT=0.022 g-s/°), agonist and antagonist muscles' tension intercept (NFIX_C=14.0 g.) that ensures an equilibrium state during an eye fixation at primary eye position, the agonist muscle's tension slope (NAG_C=0.8 g.), and the antagonist muscle's tension slope (NANT_C=0.5 g.), eye globe's inertia (J=0.000043 g-s$^2$/°). All tension characteristics may be directly impacted by the neuronal control signal sent by the brain, and therefore partially contain the neuronal control signal information.

The remaining OPC to produce the simulated saccades may be fixed to the following default values: agonist muscle neuronal control signal activation (11.7) and deactivation constants (2.0), antagonist muscle neuronal control signal activation (2.4) and deactivation constants (1.9), pulse height of the antagonist neuronal control signal (0.5 g.), pulse width of the antagonist neuronal control signal ($PW_{AG}$=7+|A| ms.), passive elasticity of the eye globe ($Kp=N_{AG\_C}-N_{ANT\_C}$) pulse height of the agonist neuronal control signal (iteratively varied to match recorded saccade's onset and offset coordinates), pulse width of the agonist neuronal control signal ($PW_{ANT}=PW_{AG}+6$).

The error function module provides high sensitivity to differences between the recorded and simulated saccade trajectories. In some cases, the error function is implemented as the absolute difference between the saccades that are recorded by an eye tracker and saccades that are simulated by the OPMM.

$$R=\Sigma_{i=1}^n |t_i-s_i|$$

where n is the number of points in a trajectory, $t_i$ is a point in a recorded trajectory and $s_i$ is a corresponding point in a simulated trajectory. The absolute difference approach may provide an advantage over other estimations such as root mean squared error (RMSE) due to its higher absolute sensitivity to the differences between the saccade trajectories.

First Example of an Experiment with Multimodal Ocular Authentication in which Only CEM & OPC Modalities are Employed The following describes an experiment including biometric authentication based on oculomotor plant characteristics and complex eye movement patterns.

Equipment. The data was recorded using the EyeLink II eye tracker at sampling frequency of 1000 Hz. Stimuli were presented on a 30 inch flat screen monitor positioned at a distance of 685 millimeters from the subject, with screen dimensions of 640×400 millimeters, and resolution of 2560× 1600 pixels. Chin rest was employed to ensure high reliability of the collected data.

Eye Movement Recording Procedure. Eye movement records were generated for participants' readings of various excerpts from Lewis Carroll's "The Hunting of the Snark." This poem was chosen for its difficult and nonsensical content, forcing readers to progress slowly and carefully through the text.

For each recording, the participant was given 1 minute to read, and text excerpts were chosen to require roughly 1 minute to complete. Participants were given a different excerpt for each of four recording session, and excerpts were selected from the "The Hunting of the Snark" to ensure the difficulty of the material was consistent, line lengths were consistent, and that learning effects did not impact subsequent readings.

Participants and Data Quality. Eye movement data was collected for a total of 32 subjects (26 males/6 females), ages 18-40 with an average age of 23 (SD=5.4). Mean positional accuracy of the recordings averaged between all calibration points was 0.74° (SD=0.54°). 29 of the subjects performed 4 recordings each, and 3 of the subjects performed 2 recordings each, generating a total of 122 unique eye movement records.

The first two recordings for each subject were conducted during the same session with a 20 minute break between recordings; the second two recordings were performed a week later, again with a 20 minute break between recordings.

Performance Evaluation. The performance of the authentication methods was evaluated via False Acceptance Rate (FAR) and False Rejection Rate (FRR) metrics. The FAR represents the percentage of imposters' records accepted as authentic users and the FRR indicates the amount of authentic users' records rejected from the system. To simplify the presentation of the results the Half Total Error Rate (HTER) was employed which was defined as the averaged combination of FAR and FRR.

Performance of authentication using biometric assessment using oculomotor plant characteristics, scanpaths, or combinations thereof, was computed as a result of a run across all possible combinations of eye movement records. For example, considering 3 eye movement records (A, B, and C) produced by unique subjects, similarity scores were produced for the combinations: A+B, A+C, B+C. For the 122 eye movement records, this resulted in 7381 combinations that were employed for acceptance and rejection tests for both methods.

For this experiment, in case of the OPC biometrics, only horizontal components of the recorded saccades with amplitudes >1° and duration over 4 ms were considered for the authentication. As a result average amplitude of the horizontal component prior to filtering was 3.42° (SD=3.25) and after filtering was 3.79° (SD=3.26). Magnitude of the vertical components prior to filtering was quite small (M=1.2° SD=3.16), therefore vertical component of movement was not considered for derivation of OPC due to high signal/noise ratio of the vertical component of movement.

Results. Table I presents results of the experiment described above. In Table I, authentication results are presented for each biometric modality. Thresholds column contains the thresholds that produce minimum HTER for the corresponding authentication approach. CUE refers to counterfeit-resistant usable eye-based authentication, which may include one of the traits, or two or more traits in combination that are based on the eye movement signal.

TABLE I

| Method Name | Thresholds | FAR | FRR | HTER |
|---|---|---|---|---|
| CUE = OPC | $p_{CUE} = 0.1$ | 30% | 24% | 27% |
| CUE = CEM | $p_{CUE} = 0.5$ | 26% | 28% | 27% |
| CUE = (OPC) OR (CEM) | $p_{OPC} = 0.8$<br>$p_s = 0.6$ | 22% | 24% | 23% |
| CUE = (OPC) AND (CEM) | $p_{OPC} = 0.1$<br>$p_s = 0.2$ | 25% | 26% | 25.5% |
| CUE = MIN(OPC, CEM) | $p_{CUE} = 0.1$ | 30% | 24% | 27% |
| CUE = MAX(OPC, CEM) | $p_{CUE} = 0.6$ | 25% | 20% | 22.5% |
| CUE = $w_1$□OPC + $w_2$□CEM | $p_{CUE} = 0.4$ | 20% | 18% | 19% |
| CUE = 0.5□(OPC) + 0.5□(CEM) | $p_{CUE} = 0.4$ | 17% | 22% | 19.5% |

Figure 5:
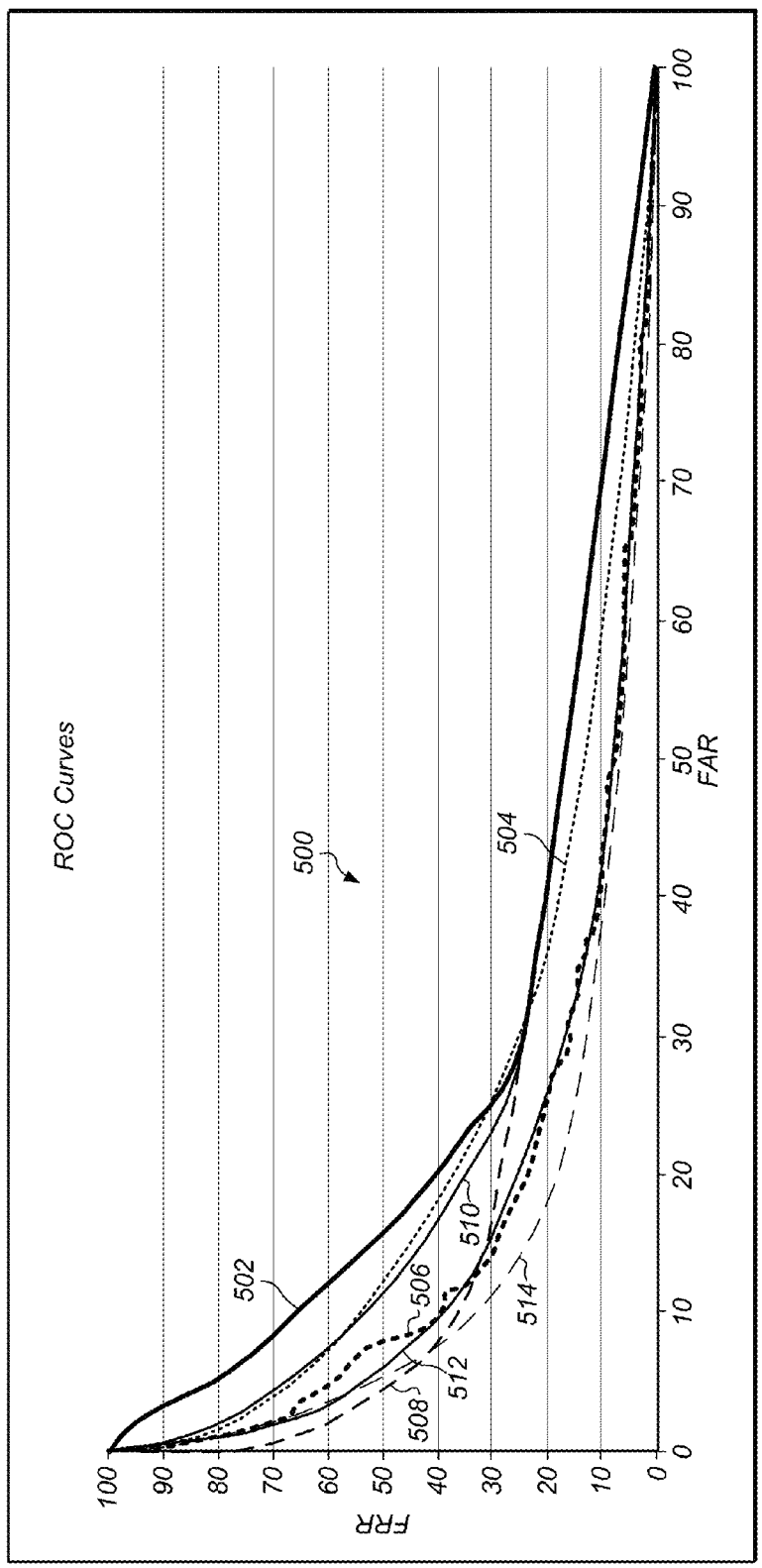
FIG. 5 is a graph illustrating receiver operating curves for ocular biometric methods in one experiment.

FIG. 5 is a graph illustrating receiver operating curves (ROC) for ocular biometric methods in the experiment described above. Each of ROC curves 500 corresponds to a different modality and/or fusion approach. Curve 502 represents an authentication based on OPC. Curve 504 represents an authentication based on CEM. Curve 506 represents an authentication based on (OPC) OR (CEM). Curve 508 represents an authentication based on (OPC) AND (CEM). Curve 510 represents an authentication based on MIN (OPC, CEM). Curve 512 represents an authentication based on MAX (OPC, CEM). Curve 514 represents an authentication based on a weighted approach w1*OPC+w2*CEM.

Results indicate that OPC biometrics can be performed successfully for a reading task, where the amplitude of saccadic eye movements can be large when compared to a jumping dot stimulus. In this example, both the OPC and CEM methods performed with similar accuracy providing the HTER of 27%. Fusion methods were able to improve the accuracy achieving the best result of 19% in case of the best performing weighted addition (weight $w_1$ was 0.45 while weight $w_2$ was 0.55). Such results may indicate approximately 30% reduction in the authentication error. In a custom case where weights for OPC and scanpath traits are equal, multimodal biometric assessment was able to achieve HTER of 19.5%.

Second Example of an Experiment with Multimodal Ocular Authentication in which Only CEM & OPC & Iris Modalities are Employed.

The following describes an experiment including biometric authentication based on oculomotor plant characteristics, complex eye movement patterns, and iris.

Equipment. Eye movement recording and iris capture were simultaneously conducted using PlayStation Eye web-camera. The camera worked at the resolution of 640×480 pixels and the frame rate of 75 Hz. The existing IR pass filter was removed from the camera and a piece of unexposed developed film was inserted as a filter for the visible spectrum of light. An array of IR lights in a form of Clover Electronics IR010 Infrared Illuminator together with two separate IR diodes placed on the body of the camera were employed for better eye tracking. The web-camera and main IR array were installed on a flexible arm of the Mainstays Halogen Desk Lamp each to provide an installation that can be adjusted to a specific user. A chin rest that was already available from a commercial eye tracking system was employed for the purpose of stabilizing the head to improve the quality of the acquired data. In a low cost scenario a comfortable chinrest can be constructed from very inexpensive materials as well. Stimulus was displayed on a 19 inch LCD monitor at a refresh rate of 60 Hz. A web camera and other equipment such as described above may provide a user authentication station at a relatively low cost.

Eye-Tracking Software. ITU eye tracking software was employed for the eye tracking purposes. The software was modified to present required stimulus and store an eye image every three seconds in addition to the existing eye tracking capabilities. Eye tracking was done in no-glint mode.

Stimulus. Stimulus was displayed on a 19 inch LCD monitor with refresh rate of 60 Hz. The distance between the screen and subjects' eyes was approximately 540 mm. The complex pattern stimulus was constructed that employed the Rorschach inkblots used in psychological examination, in order to provide relatively clean patterns which were likely to evoke varied thoughts and emotions in participants. Inkblot images were selected from the original Rorschach psychodiagnostic plates and sized/cropped to fill the screen. Participants were instructed to examine the images carefully, and recordings were performed over two sessions, with 3 rotations of 5 inkblots per session. Resulting sequence of images was 12 sec. long.

Eye movement data and iris data was collected for a total of 28 subjects (18 males, 10 females), ages 18-36 with an average age of 22.4 (SD=4.6). Each subject participated in two recording sessions with an interval of approximately 15 min. between the sessions.

Results. Weighted fusion was employed to combine scores from all three biometric modalities. The weights were selected by dividing the recorded data randomly into training and testing sets. Each set contained 50% of the original recording. After 20 random divisions the average results are presented by Table II:

TABLE II

| Method Name | Training Set - Average Performance | | | Testing Set - Average Performance | | |
|---|---|---|---|---|---|---|
| | FAR | FRR | HTER | FAR | FRR | HTER |
| Ocular Biometrics = OPC | 22% | 37% | 25.5 | 26.2% | 51.8% | 39% |
| Ocular Biometrics = CEM | 27.2% | 14.3% | 20.7% | 26.9% | 28.9 | 27.9% |
| Ocular Biometrics = Iris | 16.9% | 3.2% | 10.1% | 13.2% | 13.9% | 13.6% |
| Ocular Biometrics = $w_1$□OPC + $w_2$□CEM + $w_3$□Iris | 5.3% | 1.4% | 3.4% | 7.6% | 18.6% | 13.1% |

Figure 6:
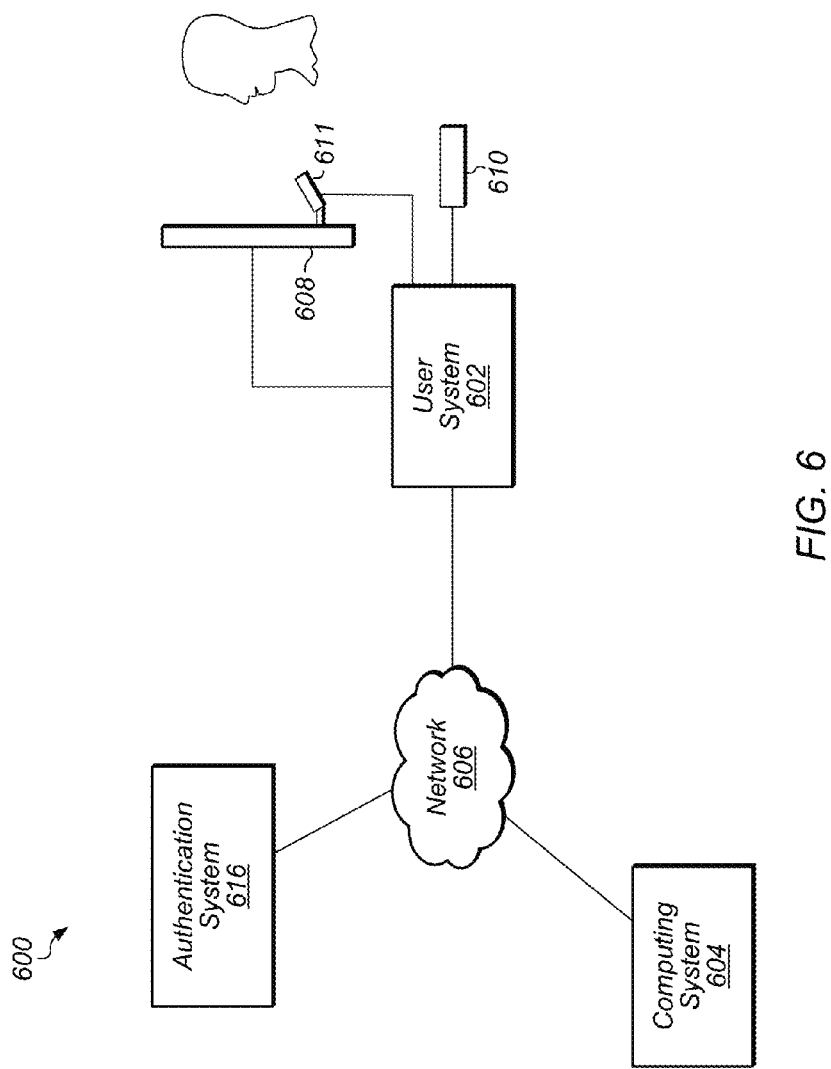
FIG. 6 illustrates one embodiment of a system for allowing remote computing with ocular biometric authentication of a user.

FIG. 6 illustrates one embodiment of a system for allowing remote computing with ocular biometric authentication of a user. System 600 includes user system 602, computing system 604, and network 606. User system 602 is connected to user display device 608, user input devices 610, and image sensor 611. Image sensor may be, for example, a web cam. User display device 608 may be, for example, a computer monitor.

Image sensor 611 may sense ocular data for the user, including eye movement and external characteristics, such as iris data and periocular information and provide the information to user system 602. Authentication system 616 may serve content to the user by way of user display device 608. Authentication system 616 may receive eye movement information, ocular measurements, or other information from user system 602. Using the information received from user system 602, authentication system 616 may assess the identity of the user. If the user is authenticated, access to computing system 604 by the user may be enabled.

In the embodiment shown in FIG. 6, user system 602, computing system 604, and authentication system 614 are shown as discrete elements for illustrative purposes. These elements may, nevertheless, in various embodiments be performed on a single computing system with one CPU, or distributed among any number of computing systems.

Figure 7:
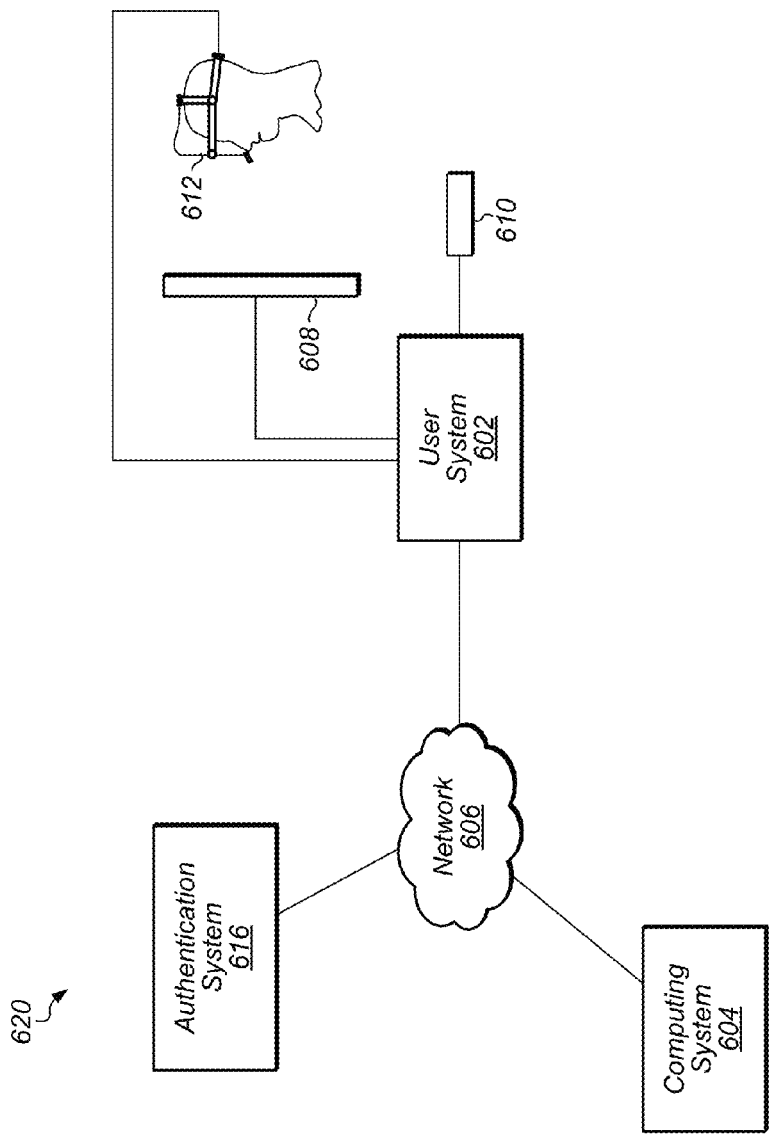
FIG. 7 illustrates one embodiment of a system for allowing remote computing with ocular biometric authentication of a user wearing an eye-tracking headgear system.

FIG. 7 illustrates one embodiment of a system for allowing remote computing with ocular biometric authentication of a user wearing an eye-tracking headgear system. System 620 may be similar to generally similar to system 600 described above relative to FIG. 6. To carry out authentication, the user may wear eye tracking device 612. Eye tracking device 612 may include eye tracking sensors for one or both eyes of the user. User system 610 may receive sensor data from eye tracking device 612. Authentication system 616 may receive information from user system 610 for authenticating the user.

Computer systems may, in various embodiments, include components such as a CPU with an associated memory medium such as Compact Disc Read-Only Memory (CD-ROM). The memory medium may store program instructions for computer programs. The program instructions may be executable by the CPU. Computer systems may further include a display device such as monitor, an alphanumeric input device such as keyboard, and a directional input device such as mouse. Computing systems may be operable to execute the computer programs to implement computer-implemented systems and methods. A computer system may allow access to users by way of any browser or operating system.

Embodiments of a subset or all (and portions or all) of the above may be implemented by program instructions stored in a memory medium or carrier medium and executed by a processor. A memory medium may include any of various types of memory devices or storage devices. The term "memory medium" is intended to include an installation medium, e.g., a Compact Disc Read Only Memory (CD-ROM), floppy disks, or tape device; a computer system memory or random access memory such as Dynamic Random Access Memory (DRAM), Double Data Rate Random Access Memory (DDR RAM), Static Random Access Memory (SRAM), Extended Data Out Random Access Memory (EDO RAM), Rambus Random Access Memory (RAM), etc.; or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network, such as the Internet. In the latter instance, the second computer may provide program instructions to the first computer for execution. The term "memory medium" may include two or more memory mediums that may reside in different locations, e.g., in different computers that are connected over a network. In some embodiments, a computer system at a respective participant location may include a memory medium(s) on which one or more computer programs or software components according to one embodiment may be stored. For example, the memory medium may store one or more programs that are executable to perform the methods described herein. The memory medium may also store operating system software, as well as other software for operation of the computer system.

The memory medium may store a software program or programs operable to implement embodiments as described herein. The software program(s) may be implemented in various ways, including, but not limited to, procedure-based techniques, component-based techniques, and/or object-oriented techniques, among others. For example, the software programs may be implemented using ActiveX controls, C++ objects, JavaBeans, Microsoft Foundation Classes (MFC), browser-based applications (e.g., Java applets), traditional programs, or other technologies or methodologies, as desired. A CPU executing code and data from the memory medium may include a means for creating and executing the software program or programs according to the embodiments described herein.

In some embodiments, collected CEM metrics are treated as statistical distributions, (rather than, for example, processing averages). In some embodiments, fusion techniques, such as random forest, are used.

Figure 8:
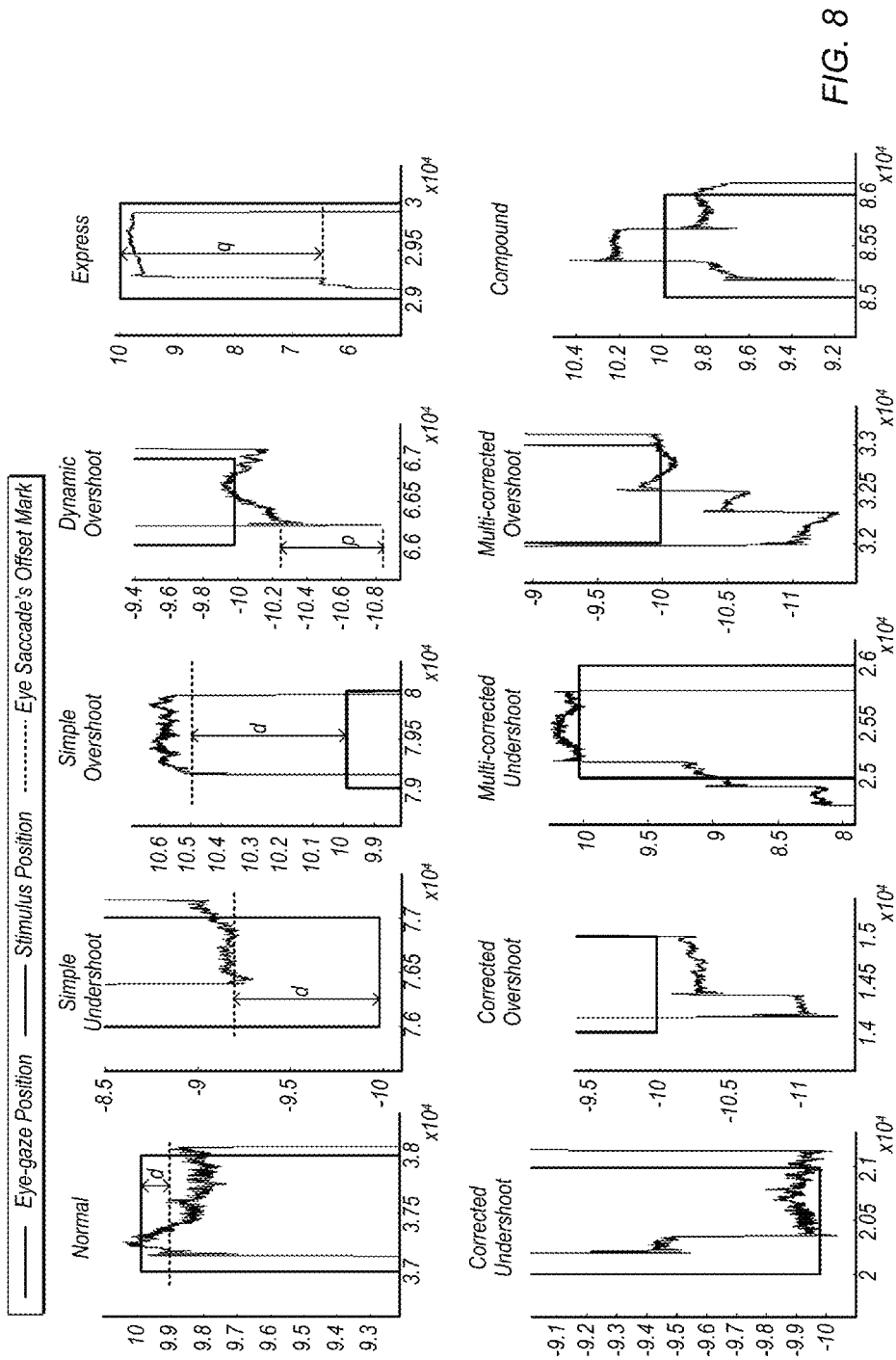
FIG. 8 is a set of graphs illustrating examples of complex oculomotor behavior.

As used herein, complex oculomotor behavior ("COB") may be considered as a subtype of basic oculomotor behavior (fixations and saccades). Metrics for COB (which is a part of the Complex Eye Movement Patterns) include simple undershoot or overshoot, corrected undershoot/overshoot, multi-corrected undershoot/overshoot, compound saccades, and dynamic overshoot. In some cases, COB may include variant forms of basic oculomotor behavior, often indicating novel or abnormal mechanics. Examples of different forms of saccadic dysmetria, compound saccades, dynamic overshoot, and express saccades are described below. FIG. 8 is a set of graphs illustrating examples of complex oculomotor behavior.

Saccadic dysmetria is a common occurrence, in which a saccade undershoots or overshoots the target stimulus. Often, if the dysmetria is too large, these saccades are followed by one or more small corrective saccades in the direction of the target. The type of dysmetria may be identified based on these characteristics: undershoot, overshoot, simple (uncorrected), corrected (1 corrective saccade), and multi-corrected (2 or more corrective saccades).

Compound saccades (also referred to as macrosaccadic oscillations) occur as a series of dysmetric saccades around a target. As such, compound saccades may be defined as a series of two or more corrective saccades occurring during a single stimulus, in which the direction of movement changes (undershoot-overshoot-undershoot, overshoot-undershoot-overshoot, etc.)

Dynamic overshoot occurs as a small (0.25° to 0.5° amplitude), oppositely directed, post-saccadic corrective movement. These post-saccadic movements may typically be merged with the preceding saccade. As such, dynamic overshoot may be identified by projecting the absolute distance travelled during the saccade onto the centroid of the previous fixation; if the projected centroid exceeds the post-saccade fixation centroid by more than 0.5° (corresponding to a minimum overshoot of 0.25°), dynamic overshoot occurred may be considered to have occurred.

Express saccades have an abnormally quick reaction time between the appearance of a stimulus and the onset of the saccade. Regular saccades may have a typical latency of 150 milliseconds; as such. As used herein, saccades with latency less than 150 milliseconds may be referred to as "express saccades".

FIG. 8 present the examples of COB. x-axis=time in milliseconds; y-axis=position in degrees). d, p, q are detection thresholds. Specific numbers relating to COB are provided herein for illustrative purposes. The COB metrics that numbers may vary from embodiment to embodiment, and spatial and temporal characteristics and the corresponding thresholds may also vary from embodiment to embodiment. In various embodiments, COB (for example, the frequency of the occurrence of various metrics that compose COB) is applied for the purposes of liveness testing, detection of the physical and the emotional state of the user of the biometric system, or both.

Biometric Liveness Testing

As used herein, a "biometric liveness test" includes a test performed to determine if the biometric sample presented to a biometric system came from a live human being. In some embodiments, a biometric liveness test is performed to determine if the biometric sample presented to the system is a live human being and is the same live human being who was originally enrolled in the system (the "authentic live human being").

In various embodiments, liveness detection built upon ocular biometrics framework is used to protect against spoof attacks. Some examples of liveness detection in response to spoofing techniques are described below. Although many of the embodiments are described for detecting to a particular spoofing technique, any of the embodiments may be applied to detect any spoofing technique.

SPOOFING EXAMPLE 1

Spoofing is Done by High-quality Iris Image Printed on Placard, Paper, Etc. and Presented to the Biometric System for the Authentication or Identification In this case, CEM (including COB) and OPC eye movement metrics are estimated. CEM related metrics may include fixation count, average fixation duration, average vectorial average vertical saccade amplitude, average vectorial saccade velocity, average vectorial saccade peak velocity, velocity waveform (Q), COB related metrics—undershot/overshoot, corrected undershoot/overshoot, multi-corrected undershoot/overshoot, dynamic, compound, express saccades, scanpath length, scanpath area, regions of interest, inflection count, and slope coefficients of the amplitude-duration and main sequence relationships; OPC—related length tension, series elasticity, passive viscosity of the agonist and the antagonist muscle, force velocity relationship, the agonist and the antagonist muscles' tension intercept, the agonist muscle's tension slope, the antagonist muscle's tension slope, eye globe's inertia, or combinations of one or more of the above. Principal component analysis and/or linear/non-linear discriminant analysis may be performed. The values of the metrics may be compared to the normal human data via statistical tests (for example, t-test, Hoteling's T-square test, MANOVA). From this analysis, a determination is made of whether a presented biometric sample is a fake or it comes from the live-authentic user.

When the spoof is presented, extracted eye metrics may have abnormal values such as zero, or be negative, or, for example, would have a linear form, when non-linear form is the norm. Abnormality examples: a) only a single fixation is detected during template acquisition and/or fixation coordinates may indicate that it is directed outside of the screen boundaries, b) no saccades are detected or saccades have the amplitudes close to zero, c) extracted OPC and CEM characteristics have abnormally small or large values.

In some embodiments, once the biometric sample presented to a biometric system is determined to have come from a live human being, a liveness test is used to determine whether the identified person is live human being who was originally enrolled in the system. Person identification of subject may be performed, for example, as described above relative to FIG. 2.

SPOOFING EXAMPLE 2

Spoofing is Done by Pre-recording Eye Movement Pattern on the Video Recording Device Such as Camera, Phone, Tablet, Etc.

In some embodiments, OPC and CEM modalities are used to extract corresponding metrics. The combination of OPC and CEM may be used even in cases when fully random stimulus is presented to the user for authentication/identification, for example, a point of light that is jumping to the random locations on the screen. Each time the pattern of what is presented to the user for authentication/identification may be different, but the person may still able to be identified by the ocular biometric system (for example, the system described in paragraph above relative to FIG. 2). Random characteristics of the stimuli may include spatial location of the presented target (for example, coordinates on the screen) and temporal pattern (for example, the time when each specific jump of the target is presented). However, if the pre-recorded sequence is presented there will be a clear spatial and temporal difference between the behavior of the stimulus and what was pre-recorded.

Figure 9:
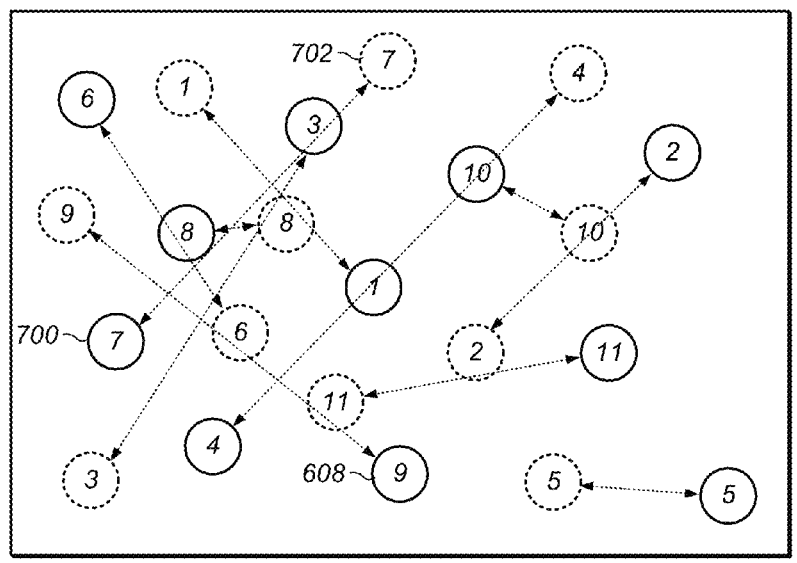
FIG. 9 illustrates a spoof attack via pre-recorded signal from the authentic user.

FIG. 9 illustrates a spoof attack via pre-recorded signal from the authentic user. In the example shown in FIG. 9, the difference between the estimated eye gaze locations from the pre-recorded signal of the authentic user (spoof) and the locations of the stimulus that may be presented during an authentication session. In this example, an intruder puts a pre-recorded video of the eye movements of the authentic user to the sensor. The biometric system randomly changes presented pattern and the estimations of the eye gaze locations from pre-recorded video miss the targets by large margins. In FIG. 9, spatial differences may be readily observed. Solid line dots 700 represent locations of points that were actually presented to the user. Broken line dots 702 represent estimated eye gaze locations that were estimated by processing pre-recorded eye movements of the authentic user to previous recorded sessions. Arrows between the pairs of dots represent positional differences between what was presented and recorded. In this case, large differences clearly indicate that the presented sample is a spoof. In some embodiments, spatial differences are checked as a Euclidian distance metric between the presented locations and recorded from the user.

Figure 10:
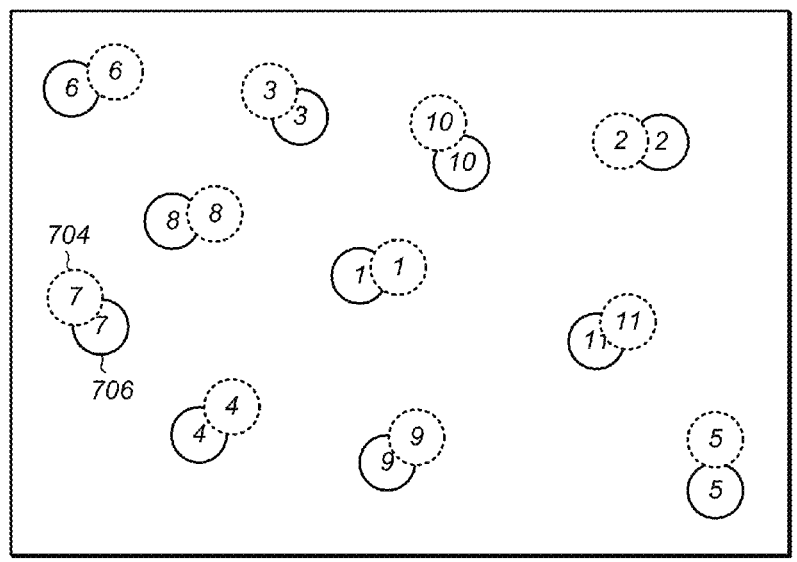
FIG. 10 illustrates eye movement for an authentic, live user.

In case of the spoof (pre-recorded eye movement sequence) the spatial and temporal difference may be large, which allows an easy distinction between the spoof and the authentic signal. For example, FIG. 10 illustrates the same figure for the authentic user. Solid line dots 704 represent locations of points that were actually presented to the user. Broken line dots 706 represent estimated eye locations from an authentic user. In the example illustrated in FIG. 10, an authentic user goes through the authentication process. Small positional differences indicate that the recorded eye is able to follow presented random stimulus and therefore it is not a pre-recorded presentation. Estimated eye gazes from the user fall very closely to presented targets, identifying that a live eye is following the targets. Thus, comparing FIG. 9 and FIG. 10, the distances between the estimated eye gazes of the spoof and what is presented as a stimulus are large, while the differences between the estimated eye gazes from the live user and the stimulus locations are small.

In some embodiments, a similar approach to biometric authentication may be applied in the time domain (for example, for biometric authentication using video). The timings of the appearances of flashing dots can be randomized and in this case pre-recorded eye movements may be out of sync temporally with what is presented on the screen, introducing large differences between stimulus onsets the movements that are pre-recorded in the video sequence.

SPOOFING EXAMPLE 3

Spoofing is Done by an Accurate Mechanical Replica of the Human Eye

In some embodiments, differences in the variability between the replica and the actual system are employed for spoof detection. To capture the variability differences between live and spoof, covariance matrixes may be built based on the OPC values estimated by an OPC biometric framework. Once such matrixes are constructed, a Principal Component Analysis (PCA) may be performed to select a subset of characteristics that contain the bulk of the variability. The resulting OPC subset may be employed to compute corresponding vector of eigen values. To make a decision if specific sample is live or a spoof, the maximum eigen value in the vector may be compared to a threshold. When a value exceeds a threshold the corresponding biometric template is marked as a spoof If the value is less than or equal to the threshold, the corresponding biometric template may be marked as live.

In the case when an intruder steals the biometric database and performs spoofing with the mechanical replica of the eye created with the knowledge of the user's biometric template, the Correct Recognition rate (correct rate of the identification of the spoof or live sample) may be approximately 85%.

In certain embodiments, a linear discriminant analysis (LDA) is performed to determine the liveness based on the metrics using the OPC biometric template. In certain embodiments, a multivariate analysis of variance (MANOVA) is performed to determine the liveness based on the metrics using the OPC biometric template.

SPOOFING EXAMPLE 4

Spoofing is Done by Imprinting High-quality Iris Image on a Contact Lens and Putting on Top of the Intruders Live Eye In a case when the iris part of the ocular biometrics system is spoofed by a contact lenses with imprinted pattern of the authentic user, the ocular biometric system may use other modalities such as OPC, CEM, and periocular features to make a distinction about the authenticity of the user. Biometric performance of all biometric modalities other than the iris may be used to determine the authenticity of the user in the case when iris modality is completely spoofed.

In some embodiments (including, for example, the embodiments described above relative to Spoofing Examples 1-4), once the biometric sample presented to a biometric system is determined to have come from a live human being, a liveness test may be used to determine whether the identified person is live human being who was originally enrolled in the system. Person identification of subject may be performed, for example, as described above relative to FIG. 2.

In some embodiments, a user indicates a coercion attack to a system via eye movement patterns. The eye movements may be pre-established before the coercion attack (for example, during training of the user). Signals by a user using eye movement patterns may be done covertly or overtly. Signals by the user to ocular biometrics system via eye tracking may be hard to detect by an intruder and will be non-intrusive. The eye tracking technology may be able to detect the direction of gaze with a precision of approximately 0.5° of the visual angle. A human, while able to tell the general location of the eye gaze and possibly count the amount of gaze shifts, cannot distinguish precisely where someone is looking.

Different types of authentication/identification stimuli such as images can be employed to allow the user to signal coercion attack in various embodiments. For example, the following types of images may be employed: a) images containing a significant amount of rich textural information across the entire image, e.g., a forest or hills, b) images containing several separate zones of attention, e.g., structures, buildings, c) images with artificial content highlighting well defined focal points, e.g., blue and red balloons.

In various examples given below, each presented image type may facilitate a login process that would allow the user to fixate his/her eyes on the distinct focal points presented on the image to signal "normal" or "coercion" attack. For example, if the image of mountains is presented during "normal" login, a user will look at the base of the hills, whereas during "coercion" entry the user will look at the pine trees.

Difference in shapes (for example, scanpaths) as drawn by the eyes (i.e. spatial and temporal differences in the eye movement signatures) may be used to determine the difference between the "coercion" and "normal login". Examples are provided below.

Figure 11:
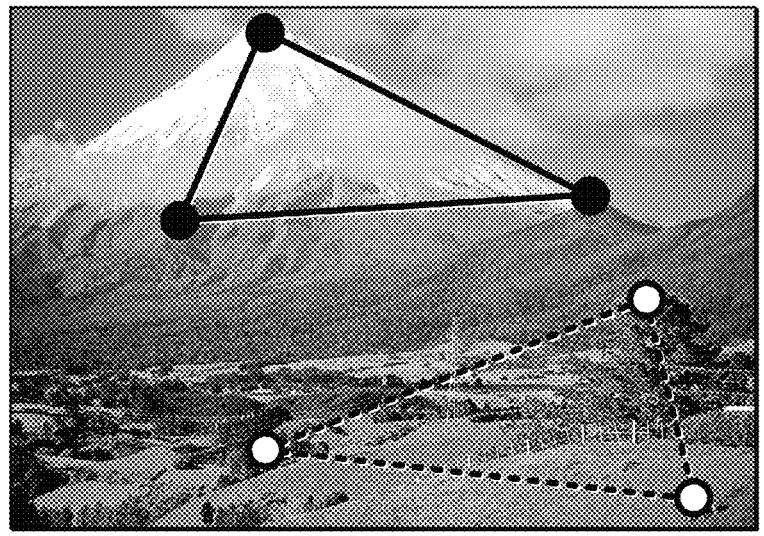
FIG. 11 illustrates an example of the difference between "normal" and "coercion" logins.

FIG. 11 illustrates an example of the difference between "normal" and "coercion" logins. The light shaded scanpath indicates the scanpath for normal login. The darker scanpath indicates the coercion login. Circles represent fixations and lines represent saccades. The spatial locations of the scanpaths may be different, however the number of fixations is the same. The intruder would not be able to notice the difference between spatial locations, because the gaze would be directed on the same screen, in the general vicinity of the presented picture. Also counting the change of the direction of the eye movement would not help, because both scanpaths have the same number of fixations and saccades that compose them.

Figure 12:
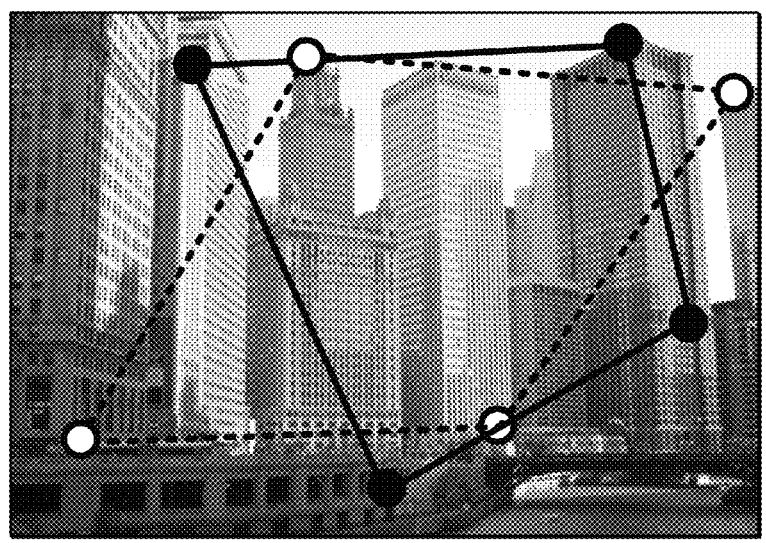
FIG. 12 illustrates a second example of the difference between "normal" and "coercion" logins.

Similarly to FIG. 11, FIG. 12 illustrates an example of the difference between "normal" and "coercion" logins. The light shaded scanpath indicates the scanpath for normal login. The darker scanpath indicates the coercion login. Circles represent fixations and lines represent saccades. The spatial locations of the scanpaths are different, however the number of fixations is the same.

It is noted that even if an intruder hacks/steals the database of the biometric templates of the system users and, for example, if the intruder knows that user has to make four fixations and four saccades to log into the system, the information would not help the intruder to detect whether the user has executed the "coercion" sequence, because this sequence also contains four fixations and four saccades and by visually observing the eye movements it would be impossible to determine which sequence a user actually executes. The intruder might count the number of rapid rotations of the eye (saccades), but not the spatial locations of the resulting fixations.

Detection of the Physical and Emotional State of the Subject

An ocular biometrics system may provide information and services in addition to determining the identity of a user. In some embodiments, the system is used to acquire information about the state of the subject. In various embodiments, indicators of the physical, emotional, health state, or whether a user is under the influence of alcohol/drugs, or a combination thereof, may be assessed.

In one embodiment, a system detects exhaustion of a user. Exhaustion detection may be beneficial to systems that are installed in user-operated machines such as cars, planes etc.

In addition to the user's identity, the system may detect fatigue and warn the user against operating machinery in such a state.

In an embodiment, an ocular biometric system detects, and assesses the severity of a traumatic brain injury or a brain trauma such as a concussion of the soldiers on the battlefield or from a sports injury (for example, when a soldier is injured as a result of the explosion or some other occurrence).

Examples of states that may be detected using an ocular biometric system include emotional states and physical states including, excessive fatigue, brain trauma, influence of substances or/and drugs, high arousal.

In some embodiments, metrics that are contained in OPC, CEM (including COB) categories are employed to detect the normality of a newly captured template. For example iris modality, periocular modality, OPC modality may indicate that user A is trying to authenticate into the system. However, metrics in the COB category may indicate excessive amount, of undershoots, overshoots, or corrective saccade. This might be the case of the excessive fatigue, because such "noisy" performance of the Human Visual System is indicative of tiredness. Fatigue may be also indicated by larger than normal amounts of express saccades and non-normal saccades in terms of their main-sequence curve (i.e., saccade will have smaller maximum velocity than during a normal saccade).

Cases of brain trauma may be detected as excessive variability present in the metrics, for example, in values of the COB metrics. Statistical tools as linear/non-linear discriminant analysis, principal component analysis, MANOVA, and other tests statistical tests may be employed to detect this excessive variability and make a decision about brain trauma. Maintaining a steady fixation against a stationary target and accurately following smooth moving target may be employed for the brain trauma detection. In such cases distance and velocity metrics may be used to determine how well the target is fixated and how closely the smoothly moving target is tracked.

Substance influence such as alcohol and drugs may be also determined by statistically processing the metrics in the CEM and OPC templates. For example number of fixations and fixation durations (both metrics are part of the CEM template) might be increased when a user is under the influence of drugs/alcohol when these metrics are compared to the already recorded values.

In case of emotion detection such as arousal fixation duration might be longer than normal, large amounts of fixations might be exhibited.

The case of excessive fatigue, brain trauma, influence of substances or/and drugs may be distinguished from the failure of liveness test. In case of user exhaustion the ocular biometric system would extract OPC, CEM (including COB) metrics, or combinations thereof, and their corresponding range would be close to normal values, even if the values are close to the top of the normal range. Extracted metrics that would fail the liveness test would likely have abnormal values, for example, negative, constant, close to zero, or values that are extremely large.

Biometric Identification via Miniature Eye Movements

In some embodiments, a system performs biometric identification using miniature eye movements. Biometric identification via miniature eye movements may be effected when a user is fixated just on a single dot. An eye movement that is called an eye fixation may be executed. Eye fixation may include three miniature eye movement types: tremor, drift, and micro-saccades (saccades with amplitudes of 0.5°). Assuming high positional and temporal resolution of an eye tracker, OPC and CEM metrics may be extracted from the micro saccades as from saccades with amplitudes larger than 0.5°. In addition, tremor characteristics such as frequency and amplitude may be employed for the person identification/authentication. Drift velocity and positional characteristics may also be employed for the person identification/authentication. In some embodiments, biometric identification via miniature eye movements is performed by the same CEM modules and is included in the regular CEM biometric template.

Biometric Identification via Saliency Maps

In some embodiments, a saliency map is generated based on recorded fixations. As used herein, a "saliency map" is a topographically arranged map that represents visual saliency of a corresponding visual scene." Fixation locations may represent highlights of the saliency maps or probabilistic distributions depending on the implementation. In the case of a static image, all fixation locations may be employed to create nodes in the saliency map. In case of the dynamic stimuli, such as video, recorded fixations may be arranged in sliding temporal windows. A separate saliency may be created for each temporal window. Saliency maps (for example, driven by the fixations and/or other features of the eye movement signal) may be stored as a part of an updated CEM template (for example, based on the approach described in FIG. 13) may be compared by statistical tests, such as Kullback-Leibler, to determine the similarity between the templates. The similarities/differences between the templates may be used to make decision about the identity of the user.

Biometric Assessment with Subject State Detection

Figure 13:
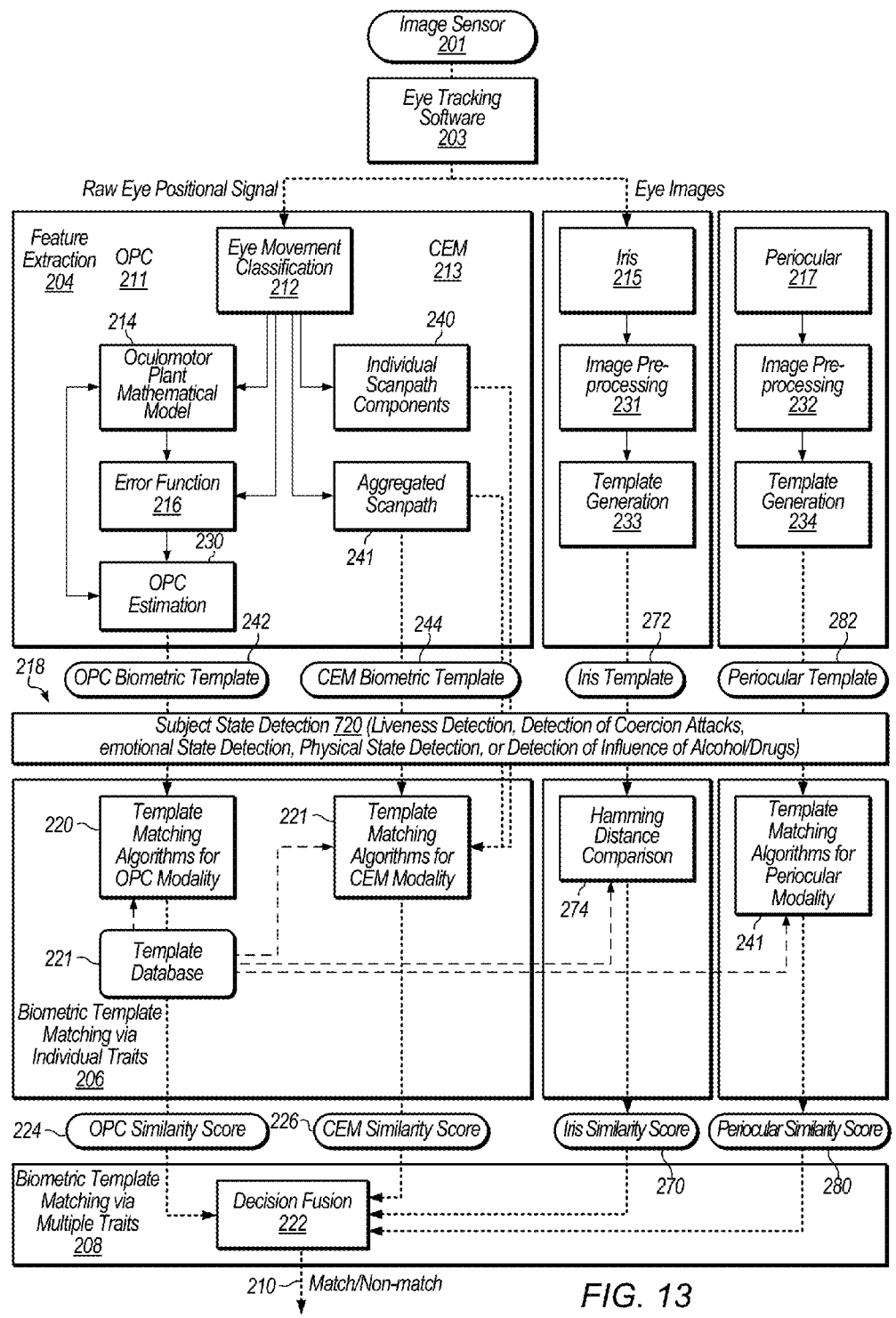
FIG. 13 illustrates biometric assessment with subject state detection and assessment.

FIG. 13 illustrates biometric assessment with subject state detection and assessment. As used herein, "subject state characteristic" includes any characteristic that can be used to assess the state of a subject. States of a subject for which characteristics may be detected and/or assessed include a subject's physical state, emotional state, condition (for example, subject is alive, subject is under the influence of a controlled substance), or external circumstances (for example, subject is under physical threat or coercion). Many of the aspects of the assessment approach shown in FIG. 13 may be carried out in a similar manner to that described above relative to FIG. 2. At 720, after biometric template generation but before biometric template matching via individual traits, state subject detection may be performed (for example, to conduct detection related to liveness, coercion, physical, emotional, health states, and the detection of the influence of the alcohol and drugs.)

In some embodiments, a decision fusion module (for example, as represented by fusion module 222 shown in FIG. 13) may perform also a liveness check in a case when one of the modalities gets spoofed (for example, the iris modality gets spoofed by the contact lens with imprinted iris pattern.)

In some embodiments, a system for person identification with biometric modalities with eye movement signals includes liveness detection. Liveness detection may include estimation and analysis of OPC. In some embodiment liveness detection is used to prevent spoof attacks (for example, spoof attacks that including generating an accurate mechanical replica of a human eye.) Spoof attack prevention may be employed for one following classes of replicas: a) replicas that are built using default OPC values specified by the research literature, and b) replicas that are built from the OPC specific to an individual.

In some embodiments, oculomotor plant characteristics (OPC) are extracted and a decision is made about the liveness of the signal based on the variability of those characteristics.

In some embodiments, liveness detection is used in conjunction with iris authentication devices is deployed in remote locations with possibly little supervision during actual authentication. Assuming that OPC capture is enabled on the existing iris authentication devices by a software upgrade such devices will have enhanced biometrics and liveness detection capabilities.

In some embodiments, a mathematical model of the oculomotor plant simulates saccades and compares them to the recorded saccades extracted from the raw positional signal. Depending on the magnitude of the resulting error between simulated and recorded saccade, an OPC estimation procedure may be invoked. This procedure refines OPC with a goal of producing a saccade trajectory that is closer to the recorded one. The process of OPC estimation may be performed iteratively until the error is minimized. OPC values that produce this minimum form become a part of the biometric template, which can be matched to an already enrolled template by a statistical test (e.g. Hotelling's T-square). Once two templates are matched, the resulting score represents the similarity between the templates. The liveness detection module checks the liveness of a biometric sample immediately after the OPC template is generated. A yes/no decision in terms of the liveness is made.

The modules used for the procedures in FIG. 13 may be implemented in a similar manner to those described relative to FIG. 2. A liveness detector and oculomotor plant mathematical models that can be employed for creating a replica of a human eye in various embodiments are described below.

Liveness Detector

The design of a liveness detector has two goals: 1) capture the differences between the live and the spoofed samples by looking at the variability of the corresponding signals, 2) reduce the number of parameters participating in the liveness decision.

Collected data indicates the feasibility of the goal one due to the substantial amount of the variability present in the eye movement signal captured from a live human and relatively low variability in the signal created by the replica. In addition to what was already stated previously about the complexity of the eye movement behavior and its variability. It is noted that the individual saccade trajectories and their characteristics may vary (to a certain extent) even in cases when the same individual makes them. This variability propagates to the estimated OPC, therefore, providing an opportunity to assess and score liveness.

To capture the variability differences between live and spoofed samples covariance matrixes may be built based on the OPC values estimated by the OPC biometric framework. Once such matrixes are constructed a Principal Component Analysis (PCA) is performed to select a subset of characteristic that contains the bulk of the variability. A resulting OPC subset is employed to compute corresponding vector of eigen values. To make a decision if specific sample is live or a spoof the maximum eigen value in the vector is compared to a threshold. When a value exceeds a threshold the corresponding biometric template is marked as a spoof and live otherwise.

Operation Modes of Eye Movement-Driven Biometric System

1. Normal Mode

In some embodiments, a video-based eye tracker is used as an eye tracking device. For each captured eye image, a pupil boundary and a corneal reflection from an IR light by the eye tracker are detected to estimate user's gaze direction.

During normal mode of operation of an eye movement-driven biometric system, a user goes to an eye tracker, represented by an image sensor and an IR light, and performs a calibration procedure. A calibration procedure may include a presentation of a jumping point of light on a display preceded by the instructions to follow the movements of the dot. During the calibration eye tracking software builds a set of mathematical equations to translate locations of eye movement features (for example, pupil and the corneal reflection) to the gaze coordinates on the screen.

The process of the biometric authentication may occur at the same time with calibration. Captured positional data during calibration procedure may be employed to verify the identity of the user. However, a separate authentication stimulus may be used following the calibration procedure if employment of such stimulus provides higher biometric accuracy.

2. Under Spoof Attack

To initiate a spoof attack, an attacker presents a mechanical replica to the biometric system. The eye tracking software may detect two features for tracking—pupil boundary and the corneal reflection. The replica follows a jumping dot of light during the calibration/authentication procedure. The movements of the replica are designed to match natural behavior of the human visual system. A template may be extracted from the recorded movements. A liveness detector analyzes the template and makes a decision if corresponding biometric sample is a spoof or not.

Mathematical Models of Human Eye

The eye movement behavior described herein is made possible by the anatomical structure termed the Oculomotor Plant (OP) and is represented by the eye globe, extraocular muscles, surrounding tissues, and neuronal control signal coming from the brain. Mathematical models of different complexities can represent the OP to simulate dynamics of the eye movement behavior for spoofing purposes. The following describes three OP models that may be employed in various embodiments.

Model I. Westheimer's second-order model represents the eye globe and corresponding viscoelasticity via single linear elements for inertia, friction, and stiffness. Individual forces that are generated by the lateral and medial rectus are lumped together in a torque that is dependent on the angular eye position and is driven by a simplified step neuronal control signal. The magnitude of the step signal is controlled by a coefficient that is directly related to the amplitude of the corresponding saccade.

OPC employed for simulation. Westheimer's model puts inertia, friction, and stiffness in direct dependency to each other. In the experiments described herein, only two OPC—stiffness coefficient and step coefficient of the neuronal control signal—were varied to simulate a saccade's trajectory.

Model II. A fourth-order model proposed by Robinson employs neuronal control signal in a more realistic pulse-step form, rather than simplified step form. As a result the model is able to simulate saccades of different amplitudes and durations, with realistic positional profiles. The model breaks OPC into two groups represented by the active and passive components. The former group is represented by the force-velocity relationship, series elasticity, and active state tension generated by the neuronal control signal. The latter group is represented by the passive components of the orbit and the muscles in a form of fast and slow viscoelastic elements. All elements may be approximated via linear mechanical representations (for example, linear springs and voigt elements.)

OPC employed for simulation. In experiments described herein, the following six parameters were employed for saccade's simulation in the representation: net muscle series elastic stiffness, net muscle force-velocity slope, fast/slow passive viscoelastic elements represented by spring stiffness and viscosity.

Model III is a fourth-order model by Komogortsev and Khan, which is derived from an earlier model of Bahill. This model represents each extraocular muscle and their internal forces individually with a separate pulse-step neuronal control signal provided to each muscle. Each extraocular muscle can play a role of the agonist—muscle pulling the eye globe and the antagonist—muscle resisting the pull. The forces inside of each individual muscle are: force-velocity relationship, series elasticity, and active state tension generated by the neuronal control signal. The model lumps together passive viscoelastic characteristics of the eye globe and extraocular muscles into two linear elements. The model is capable of generating saccades with positional, velocity, and acceleration profiles that are close to the physiological data and it is able to perform rightward and leftward saccades from any point in the horizontal plane.

OPC extracted for simulation: In experiments described herein, eighteen OPC were employed for the simulation of a saccade: length tension relationship, series elasticity, passive viscosity, force velocity relationships for the agonist/antagonist muscles, agonist/antagonist muscles' tension intercept, the agonist muscle's tension slope, and the antagonist muscle's tension slope, eye globe's inertia, pulse height of the neuronal control signal in the agonist muscle, pulse width of the neuronal control signal in the agonist muscle, four parameters responsible for transformation of the pulse step neuronal control signal into the active state tension, passive elasticity.

Experiment with Human Eye Replicas

Spoof attacks were conducted by the mechanical replicas simulated via three different mathematical models representing human eye. The replicas varied from relatively simple ones that oversimplify the anatomical complexity of the oculomotor plant to more anatomically accurate ones. Two strategies were employed for the creation of the replicas. The first strategy employed values for the characteristics of the oculomotor plant taken from the literature and the second strategy employed exact values of each authentic user. Results indicate that a more accurate individualized replica is able to spoof eye movement-driven system more successfully, however, even in this error rates were relatively low, i.e., FSAR=4%, FLRR=27.4%.

For spoofing purposes, a replica was made to exhibit most common eye movement behavior that includes COB events. These events and their corresponding parameters are illustrated by FIG. 8 and described below.

In this example, the onset of the initial saccade to the target occurs in a 200-250 ms temporal window, representing typical saccadic latency of a normal person. Each initial saccade is generated in a form of undershoot or overshoot with the resulting error of random magnitude (p2) not to exceed 2° degrees of the visual angle. If the resulting saccade's offset (end) position differs from the stimulus position by more than 0.5° (p3) a subsequent corrective saccade is executed. Each corrective saccade is performed to move an eye fixation closer to the stimulus with the resulting error (p4) not to exceed 0.5°. The latency (p5) prior to a corrective saccade is randomly selected in a range 100-130 ms. The durations of all saccades is computed via formula 2.2 DOT A+21, where A represents saccade's amplitude in degrees of the visual angle.

To ensure that spoofing attack produces accurate fixation behavior following steps are taken: 1) random jitter with amplitude (p6) not to exceed 0.05° is added to simulate tremor, 2) blink events are added with characteristics that resemble human behavior and signal artifacts produced by the recording equipment prior and after blinks. The duration (p7) of each blink is randomly selected from the range 100-400 ms. Time interval between individual blinks is randomly selected in the 14-15 sec. temporal window. To simulate signal artifacts introduced by the eye tracking equipment prior and after the blink, the positional coordinates for the eye gaze samples immediately preceding and following a blink are set to the maximum allowed recording range (±30° in our setup).

During a spoof attack, in this experiment, only horizontal components of movement are simulated. While generation of vertical and horizontal components of movement performed by the HVS can be fully independent, it is also possible to witness different synchronization mechanisms imposed by the brain while generating oblique saccades. Even in cases when a person is asked to make purely horizontal saccades it is possible to detect vertical positional shifts in a form of jitter and other deviations from purely horizontal trajectory. Consideration and simulation of the events present in the vertical component of movement would introduce complexity into the modeling process.

The goal of the stimulus was to invoke a large number of horizontal saccades to allow reliable liveness detection. The stimulus was displayed as a jumping dot, consisting of a grey disc sized approximately 1° with a small black point in the center. The dot performed 100 jumps horizontally. Jumps had the amplitude of 30 degrees of the visual angle. Subjects were instructed to follow the jumping dot.

Two strategies that may be employed by an attacker to generate spoof samples via described oculomotor plant models as described as follows: The first strategy assumes that the attacker does not have access to the stored OPC biometric template data. In this case the attacker employs the default OPC values taken from the literature to build a single mechanical replica of the eye to represent any authentic user. The second strategy assumes that the attacker has stolen the database with stored OPC biometric templates and can employ OPC values to produce a personalized replica for each individual to ensure maximum success of the spoof attack. In this case a separate replica is built for each individual by employing OPC averages obtained from the OPC biometric templates generated from all recordings of this person.

As a result the following spoofing attacks were considered. Spoof I-A and Spoof II-A represent the attacks performed by the replica created by the Model I and Model II respectively employing the first spoof generation strategy. Spoofs for the Models I and II created by the second strategy (i.e., Spoofs I-B, II-B), were not considered because if the corresponding OPC for the model I and II are derived from the recorded eye movement signal, then the saccades generated with resulting OPC are very different from normally exhibited saccades. Model III allows creating human-like saccades for both strategies, therefore producing attacks Spoof III-A and III-B.

The following metrics are employed for the assessment of liveness detection and resistance to spoofing attacks.

$$CR = 100 \cdot \frac{\text{Correctly Classified Samples}}{\text{Total Amount Of Samples}} \qquad 1$$

Here CR is Classification Rate. CorrectlyClassifiedSamples is the number of tests where OPC set was correctly identified as spoof or live. TotalAmountOfSamples is the total number of classified samples.

$$FSAR = 100 \cdot \frac{\text{Improper Classified Spoof Samples}}{\text{Total Amount Of Spoof Samples}} \quad (2)$$

Here FSAR is False Spoof Acceptance Rate. ImproperClassifiedSpoofSamples is the number of spoof samples classified as live and TotalAmountOfSpoofSamples is the total amount of spoofed samples in the dataset.

$$FLRR = 100 \cdot \frac{\text{Improper Classified Live Samples}}{\text{Total Amount Of Live Samples}} \quad (3)$$

Here FLRR is False Live Rejection Rate. ImproperClassifiedLiveSamples is the number of live samples that was marked by liveness detector as a spoof and TotalAmountOfLiveSamples is the total amount of live records in the dataset.

Table I shows results of the spoof detection experiment. Numbers in the table represent percentages. "SD" represents standard deviation. The signal from live humans was captured at 1000 Hz with a high-grade commercial eye tracking equipment, providing an opportunity to obtain the OPC from a very high quality eye positional signal. The signal from the replica was generated also at a frequency of 1000 Hz.

TABLE I

| Spoof | CR (SD) | FSAR (SD) | FLRR (SD) | EER |
|---|---|---|---|---|
| I-A | 93 (3.9) | 0 (0) | 7.4 (4.1) | 5 |
| II-A | 80.3 (25.2) | 0 (0) | 11.8 (7) | 8 |
| III-A | 86.4 (4.2) | 0 (0) | 15.5 (4.6) | 17 |
| III-B | 84.7 (4.1) | 4 (5.2) | 27.4 (4.1) | 20 |

Biometric Assessment Using Statistical Distributions

In some embodiments, biometric techniques using on patterns identifiable in human eye movements are used to distinguish individuals. The distribution of primitive eye movement features is determined using algorithms based on one or more statistical tests. In various embodiments, the statistical tests may include a Ansari-Bradley test, a Mann-Whitney U-test, a two-sample Kolmogorov-Smirnov test, a two-sample t-test, or a two-sample Cramér-von Mises test. Score-level information fusion may be applied and evaluated by one or more of the following: weighted mean, support vector machine, random forest, and likelihood ratio.

The distribution of primitive features inherent in basic eye movements can be utilized to uniquely identify a given individual. Several comparison algorithms may be evaluated based on statistical tests for comparing distributions, including: the two-sample t-test, the Ansari-Bradley test, the Mann-Whitney U-test, the two-sample Kolmogorov-Smirnov test, and the two-sample Cramér-von Mises test. Information fusion techniques may include score-level fusion by: weighted mean, support vector machine, random forest, and likelihood ratio.

CEM Biometric Framework

In one embodiment, a biometric assessment includes sensing, feature extraction, quality assessment matching, and decision making. In one embodiment, different stages of the assessment are carried out in different modules. In one embodiment, a Sensor module processes the eye movement signal, a Feature Extraction module identifies, filters, and merges individual gaze points into fixations and saccades, a Quality Assessment module assesses the biometric viability of each recording, a Matching module generates training/testing sets and compares individual recordings, and a Decision module calculates error rates under biometric verification and identification scenarios. These modules may be as further described below.

Sensor Module

The Sensor module may parse individual eye movement recordings, combining available left/right eye coordinates and removing invalid data points from the eye movement signal. Eye movement recordings are stored in memory as an eye movement database, with the eye movement signal linked to the experiment, trial, and subject that generated the recording.

Feature Extraction Module

The Feature Extraction module may generate feature templates for each record in the eye movement database. Eye movement features are primarily composed of fixations and saccades. The eye movement signal is parsed to identify fixations and saccades using an eye movement classification algorithm, followed by micro-saccade and micro-fixation filters.

Fixation and saccade groups are merged, identifying fixation-specific and saccade-specific features. Fixation features include: start time, duration, horizontal centroid, and vertical centroid. Saccade features include: start time, duration, horizontal amplitude, vertical amplitude, average horizontal velocity, average vertical velocity, horizontal peak velocity, and vertical peak velocity.

Quality Assessment Module

The Quality Assessment may module identify the biometric viability of the generated feature templates. In this context, we utilize the fixation quantitative score, ideal fixation quantitative score, fixation qualitative score, and saccade quantitative score as tentative measure of the quality of features obtained from the recording.

Matching Module

The Matching module compares individual records, generating match scores for various metrics using comparison algorithms that operate on feature templates. In this case, comparison algorithms operate to compare the distribution of fixation- and saccade-based features throughout each record. Match scores from each comparison algorithm are then combined into a single match score with an information fusion algorithm.

The Matching module may partition records, splitting the database into training and testing sets by subject, according to a uniformly random distribution. Comparison and information fusion thresholds and parameters are generated on the training set, while error rates are calculated on the testing set.

Decision Module

The Decision module may calculate error rates for comparison and information fusion under biometric verification and identification scenarios. Under one verification scenario, each record in the testing set may be compared to every other record in the testing set exactly once, and false acceptance rate and true positive rate are calculated at varied acceptance thresholds. Under one identification scenario, every record in the testing set may be compared to every other record in the testing set, and identification rates are calculated from the largest match score(s) from each of these comparison sets.

CEM Biometrics

In some embodiments, the following primitive eye movement may be assessed:
  Start time (fixation)
  Duration (fixation)
  Horizontal centroid (fixation)
  Vertical centroid (fixation)
  Start time (saccade)

Duration (saccade)
Horizontal amplitude (saccade)
Vertical amplitude (saccade)
Horizontal mean velocity (saccade)
Vertical mean velocity (saccade)
Horizontal peak velocity (saccade)
Vertical peak velocity (saccade)

Figure 14:
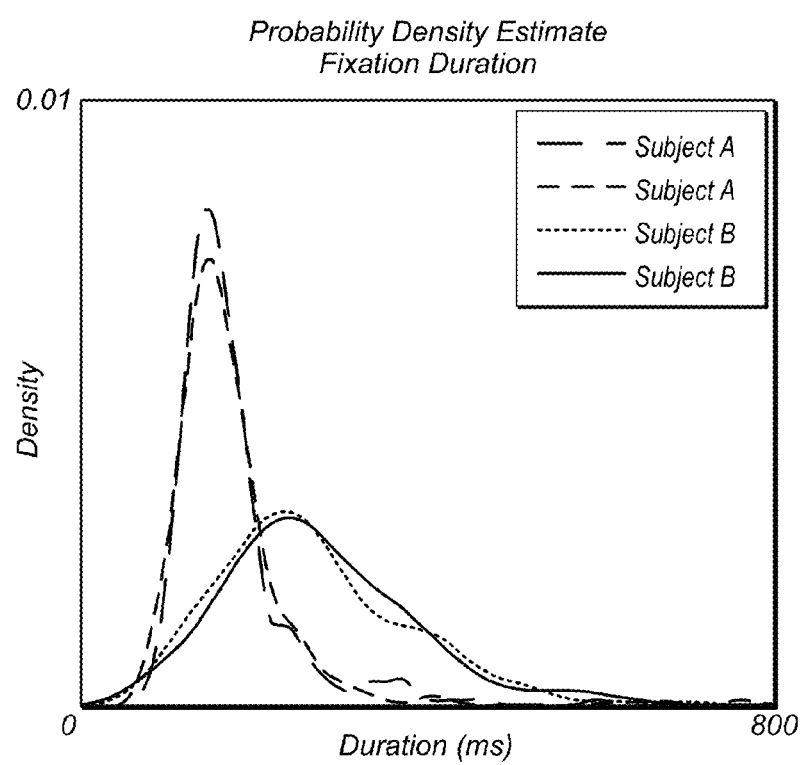
FIG. 14 illustrates a comparative distribution of fixation over multiple recording sessions.

These features accumulate over the course of a recording, as the scanpath is generated. FIG. 14 illustrates a comparative distribution of fixation over multiple recording sessions. By analyzing the distribution of these features throughout each recording, as shown in FIG. 14, the behavior of the scanpath as a whole may be examined. At the same time, by considering the fixations and saccades that compose the scanpath, signal noise from the raw eye movement signal may be removed, and the dataset reduced to a computationally manageable size.

In some embodiments, to compare the distribution of primitive eye movement features, multiple statistical tests are employed. These statistical tests are applied as a comparison algorithm to the distributions of each feature separately. The information fusion algorithms may be applied to the match scores generated by each comparison algorithm to produce a single match score used for biometric authentication.

The following are some comparison algorithms that may be applied in various embodiments.

(C1) Two-Sample t-Test

The two-sample t-test measures the probability that observations from two recordings are taken from normal distributions with equal mean and variance.

(C2) Ansari-Bradley Test

The Ansari-Bradley test measures the probability that observations from two recordings with similar median and shape are taken from distributions with equivalent dispersion.

(C3) Mann-Whitney U-Test

The Mann-Whitney U-test measures the probability that observations from two recordings are taken from continuous distributions with equal median.

(C4) Two-Sample Kolmogorov-Smirnov Test

The two-sample Kolmogorov-Smirnov test measures the probability that observations from two recordings are taken from the same continuous distribution, measuring the distance between empirical distributions.

(C5) Two-Sample Cramér-von Mises Test

The two-sample Cramér-von Mises test measures the probability that observations from two recordings are taken from the same continuous distribution, measuring the goodness-of-fit between empirical distributions.

The following are some information fusion algorithms that may be applied in various embodiments.

(F1) Weighted Mean

The weighted mean algorithm combines the match scores produced for individual metrics into a single match score on the interval $[0, 1]$. The genuine and imposter match score vectors of the training set are used to select per-metric weighting which minimizes equal error rate via iterative optimization, and the weighted mean produces a single match score as a linear combination of the match scores for each metric.

(F2) Support Vector Machine

The support vector machine algorithm classifies the match scores produced for individual metrics into a single match score in the set $\{0, 1\}$. The support vector machine builds a 7th order polynomial on the genuine and imposter match score vectors of the training set, and match scores are classified by dividing them into categories separated by the polynomial on an n-dimensional hyperplane.

(F3) Random Forest

The random forest algorithm combines the match scores produced for individual metrics into a single match score on the interval $[0, 1]$. An ensemble of 50 regression trees is built on the genuine and imposter match score vectors of the training set, and the random forest calculates the combined match score based on a set of conditional rules and probabilities.

(F4) Likelihood Ratio

The likelihood ratio algorithm combines the match scores produced for individual metrics into a single match score on the interval $\{0, 1\}$. The genuine and imposter match score vectors of the training set are modeled using Gaussian mixture models, and the likelihood ratio is calculated as the ratio of the genuine probability density over the imposter probability density.

Experiment to Evaluate Biometric Techniques

The following describes an experiment to evaluate biometric techniques. Biometric accuracy on both high- and low-resolution eye tracking systems were used. Existing eye movement datasets collected by Komogortsev were utilized for comparative evaluation, with collection methodology in the following subsections.

Eye movement recordings were generated on both high-resolution and low-resolution eye tracking systems using a textual stimulus pattern. The text of the stimulus was taken from Lewis Carroll's poem, "The Hunting of the Snark," chosen for its difficult and nonsensical content, forcing readers to progress slowly and carefully through the text.

For each recording session, subjects were limited to 1 minute of reading. To reduce learning effects, subjects were given a different excerpt from the text for each recording session and each excerpt was selected to ensure that line lengths and the difficulty of material were consistent. As well, excerpts were selected to require approximately 1 minute of active reading.

Eye movements were processed with the biometric framework described above, with eye movement classification thresholds: velocity threshold of 20°/sec, micro-saccade threshold of 0.5°, and micro-fixation threshold of 100 milliseconds. Feature extraction was performed across all eye movement recordings, while matching and information fusion were performed according to the methods described in herein. To assess biometric accuracy, error rates were calculated under both verification and identification scenarios.

Eye movement recordings were partitioned, by subject, into training and testing sets according to a uniformly random distribution with a ratio of 1:1, such that no subject had recordings in both the training and testing sets. Experimental results are averaged over 80 random partitions for each metric, and 20 random partitions for each fusion algorithm. Scores for the best performing algorithms are highlighted for readability.

1. Verification Scenario

Figure 15A:
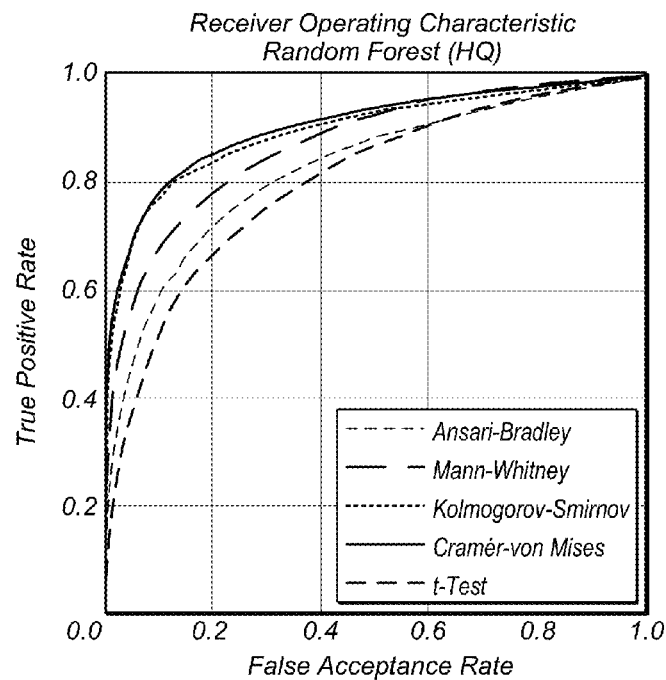
FIGS. 15A and 15B are graphs of a receiver operating characteristic in which true positive rate is plotted against false acceptance rate for several fusion methods.
Figure 15B:
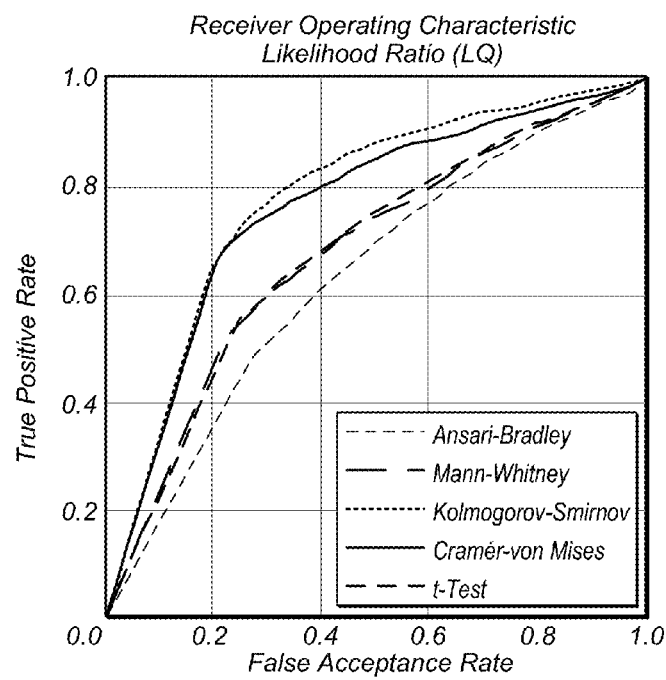

False acceptance rate is defined as the rate at which imposter scores exceed the acceptance threshold, false rejection rate is defined as the rate at which genuine scores fall below the acceptance threshold, and true positive rate is defined as the rate at which genuine scores exceed the acceptance threshold. The equal error rate is the rate at which false acceptance rate and false rejection rate are equal. FIGS. 15A and 15B are graphs of the receiver operating characteristic in which true positive rate is plotted against false acceptance rate for several fusion methods. FIG. 15A is based on high resolution recordings. FIG. 15B is based on low resolution recordings.

2. Identification Scenario

Figure 16A:
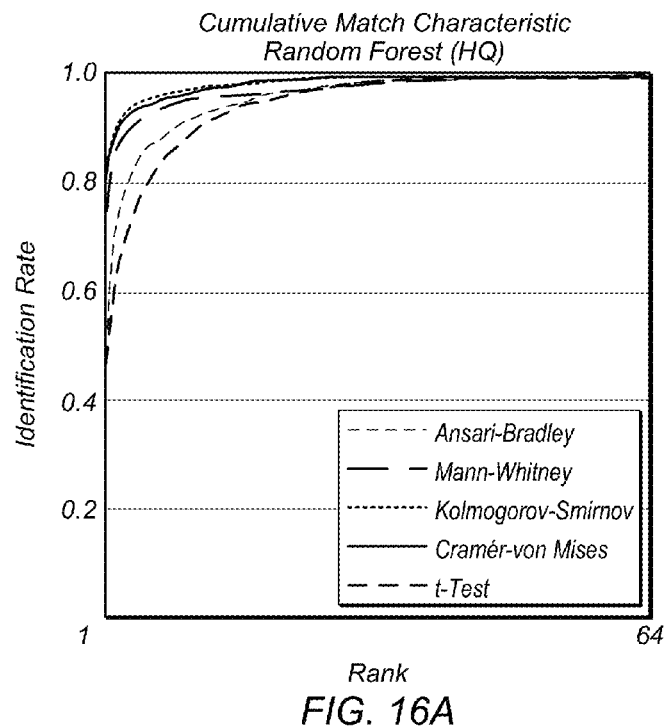
FIGS. 16A and 16B are graphs of a cumulative match characteristic for several fusion methods.
Figure 16B:
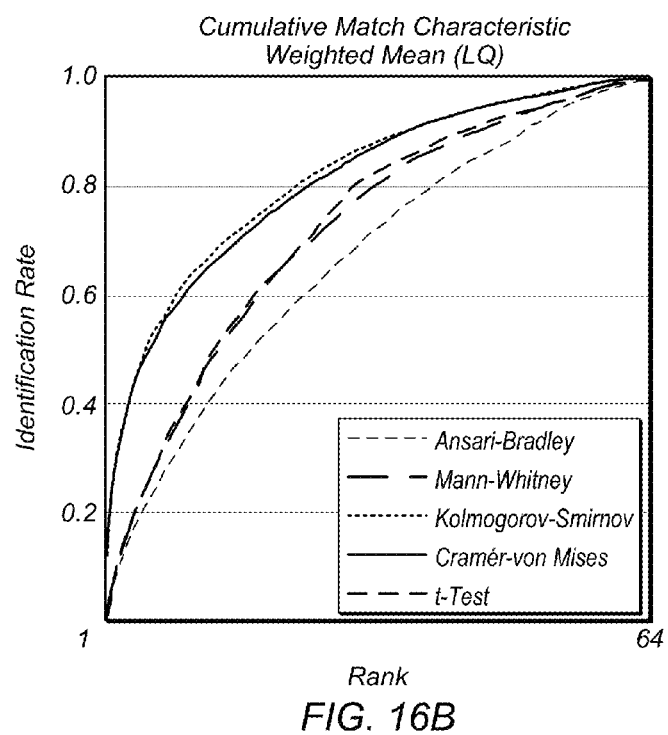

Identification rate is defined as the rate at which enrolled subjects are successfully identified as the correct individual, where rank-k identification rate is the rate at which the correct individual is found within the top k matches. FIGS. 16A and 16B are graphs of the cumulative match characteristic for several fusion methods, in which identification rate by rank is plotted across all ranks The maximum rank is equivalent to the available comparisons. FIG. 16A is based on high resolution recordings. FIG. 16B is based on low resolution recordings.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Methods may be implemented manually, in software, in hardware, or a combination thereof. The order of any method may be changed, and various elements may be added, reordered, combined, omitted, modified, etc. Changes may be made in the elements described herein without departing from the spirit and scope of the invention as described in the following claims.

What is claimed is:

1. A method of assessing a person's identity, comprising:
   measuring eye movement of the person;
   estimating one or more anatomical characteristics of an oculomotor plant of the person based at least in part on at least a portion of the measured eye movement;
   estimating one or more brain's control strategies in guiding visual attention via exhibition of complex eye movement patterns represented in part by spatial paths of the eye computed from the measured eye movement; and
   assessing the person's identity based in part on at least one of the estimated one or more characteristics of the oculomotor plant of the person, and based in part on one or more properties related to the complex eye movement patterns.

2. The method of claim 1, wherein measuring eye movement of the person comprises eye tracking.

3. The method of claim 1, wherein estimating at least one of the anatomical characteristics of an oculomotor plant of the person comprises creating a two-dimensional mathematical model including at least one of the anatomical characteristics of the oculomotor plant.

4. The method of claim 1, further comprising generating one or more brain's control strategies in guiding visual attention from eye movements of the person in a form of complex eye movement patterns, wherein the assessment of the person's identity is based in part on one or more components of complex eye movement patterns.

5. The method of claim 1, wherein assessing the person's identity comprises matching the biometric templates related to complex eye movement patterns and oculomotor plant characteristics with previously acquired templates for the person.

6. The method of claim 1, wherein assessing the person's identity comprises determining the identity of the person.

7. The method of claim 1, wherein further comprising authenticating the person based on the assessment of the person's identity.

8. The method of claim 1, wherein estimating at least one of the one or more characteristics of an oculomotor plant of the person comprises estimating at least one static characteristic of the oculomotor plant.

9. The method of claim 1, wherein estimating at least one of the one or more characteristics of an oculomotor plant of the person comprises estimating at least one dynamic characteristic of the oculomotor plant.

10. The method of claim 1, further comprising measuring one or more external characteristics of at least one eye of the person, wherein the assessment of the person's identity is based in part on at least one of the measured characteristics.

11. The method of claim 10, wherein measuring one or more external characteristics comprises measuring one or more characteristics of an iris or a periocular region of the eye of the person.

12. The method of claim 10, wherein measuring one or more external characteristics comprises measuring one or more characteristics of an iris and one or more characteristics of a periocular region of the eye of the person.

13. The method of claim 1, wherein at least some measurements of eye movement of the person are performed while the person is reading, looking at images, webpages, or interacting with a computer, wherein estimating at least one of the one or more characteristics of the oculomotor plant of the person is based on measured eye movement while the person is reading, looking at images, webpages, or interacting with a computer.

14. The method of claim 1, further comprising accessing one or more oculomotor plant characteristic templates for the person, wherein the assessment of the person's identity is based in part on a comparison of eye movement with at least one of the one or more oculomotor plant characteristic templates.

15. The method of claim 1, wherein at least one of the oculomotor plant characteristic templates is based at in part on previous measurements of eye movement of the person.

16. The method of claim 1, wherein at least one estimate of the one or more characteristics of the oculomotor plant of the person is based at least in part on an oculomotor plant mathematical model.

17. The method of claim 1, further comprising producing a minimum error between one or more recorded signals and one or more simulated signals.

18. The method of claim 1, wherein assessing the person's identity comprises applying one or more statistical tests to one or more oculomotor plant characteristics.

19. A system, comprising:
   an instrument configured to measure eye movement of a person and one or more characteristics of an eye of the person; and
   a processor;
   a memory coupled to the processor, wherein the memory comprises program instructions executable by the processor to implement:
   measuring eye movement of the person with the instrument;
   estimating one or more characteristics of an oculomotor plant of the person based at least in part on at least a portion of the measured eye movement;
   estimating one or more properties of the complex eye movement patterns based at least in part on at least a portion of the measured eye movement; and assessing the person's identity based in part on at least one of the estimated one or more characteristics of the oculomotor plant of the person, and based in part on at least one of the estimated one or more complex eye movement patterns.

20. A non-transitory, computer-readable storage medium comprising program instructions stored thereon, wherein the program instructions are configured to implement:

measuring eye movement of the person;

estimating one or more characteristics of an oculomotor plant of the person based at least in part on at least a portion of the measured eye movement;

estimating one or more complex eye movement patterns of the eye based at least in part on at least a portion of the measured eye movement; and assessing the person's identity based in part on at least one of the estimated one or more characteristics of the oculomotor plant of the person, and based in part on at least one of the estimated one or more complex eye movement patterns of the eye.

* * * * *

UNITED STATES PATENT AND TRADEMARK OFFICE
CERTIFICATE OF CORRECTION

PATENT NO. : 9,082,011 B2
APPLICATION NO. : 13/908748
DATED : July 14, 2015
INVENTOR(S) : Oleg V. Komogortsev Page 1 of 1

It is certified that error appears in the above-identified patent and that said Letters Patent is hereby corrected as shown below:

In the Specification

Lines 15 - 22, Column 1, delete the following text:
"This invention was made with government support under award no. 60NANB10D213 awarded by the National Institute of Standards, the National Science Foundation CAREER Grant #CNS-1250718, the National Institute of Standards and Technology Grants #60NANB10D213 and #60NANB12D234, and the National Science Foundation GRFP Grant #DGE-1144466. The government has certain rights in the invention."

Insert the following text:
-- This invention was made with government support under award nos. 60NANB10D213 and 60NANB12D234 awarded by the National Institute of Standards and Technology and grant nos. CNS1250718 and DGE1144466 awarded by the National Science Foundation. The government has certain rights in the invention. --

Signed and Sealed this
Eleventh Day of February, 2025

Coke Morgan Stewart
*Acting Director of the United States Patent and Trademark Office*